(12) United States Patent
Bernardon

(10) Patent No.: US 6,313,162 B1
(45) Date of Patent: Nov. 6, 2001

(54) PROPYNYL OR DIENYL BIAROMATIC COMPOUNDS

(75) Inventor: Jean-Michel Bernardon, Le Rouret (FR)

(73) Assignee: Centre International de Recherche Dermatologiques Galderma (C.I.R.D.) Galderma, Valbonne (FR)

( * ) Notice: Subject to any disclaimer, the term of this patent is extended or adjusted under 35 U.S.C. 154(b) by 0 days.

(21) Appl. No.: 09/466,230

(22) Filed: Dec. 17, 1999

Related U.S. Application Data

(62) Division of application No. 08/952,302, filed as application No. PCT/FR97/00390 on Mar. 5, 1997, now Pat. No. 6,046,220.

(30) Foreign Application Priority Data

Mar. 14, 1996 (FR) .................................... 96 03234

(51) Int. Cl.[7] .................. A61K 31/38; A61K 31/35; C07D 335/04; C07D 311/04
(52) U.S. Cl. .................. 514/432; 514/456; 549/23; 549/28; 549/398; 549/399
(58) Field of Search ........................ 514/432, 456; 549/23, 28, 398, 399

(56) References Cited

U.S. PATENT DOCUMENTS

| | | | | |
|---|---|---|---|---|
| 5,391,766 | * | 2/1995 | Klaus et al. ........................ | 549/23 |
| 5,455,265 | * | 10/1995 | Chandraratna ........................ | 514/448 |
| 5,837,725 | * | 11/1998 | Dawson et al. ........................ | 514/467 |
| 6,090,826 | * | 7/2000 | Chandraratna ........................ | 514/337 |

FOREIGN PATENT DOCUMENTS 0 661 258    7/1995    (EP) .

* cited by examiner

Primary Examiner—Deborah C. Lambkin
(74) Attorney, Agent, or Firm—Burns, Doane, Swecker & Mathis, L.L.P.

(57) ABSTRACT

The invention relates to novel propynyl or dienyl biaromatic compounds which have the general formula (I)

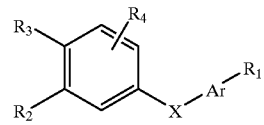

(I)

Figure 1:
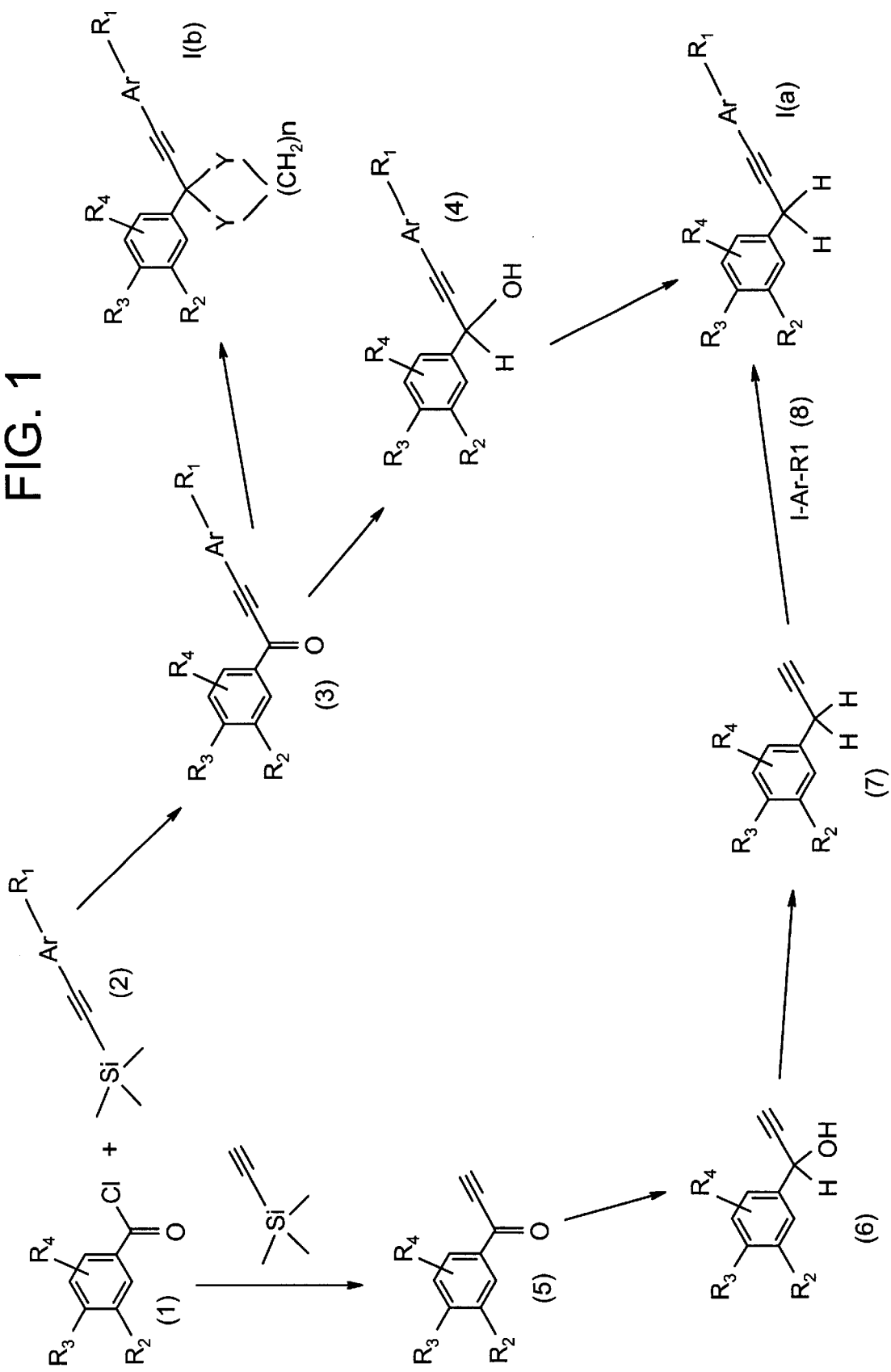

as well as to the use of these compounds in pharmaceutical compositions intended for use in human or veterinary medicine (dermatological, rheumatic, respiratory, cardiovascular and ophthalmological complaints in particular), or alternatively in cosmetic compositions.

31 Claims, 3 Drawing Sheets

PROPYNYL OR DIENYL BIAROMATIC COMPOUNDS

This application is a divisional of application Ser. No. 08/952,302, filed Jan. 26, 1998, now U.S. Pat. No. 6,046,220, which is a 371 of PCT/FR97/00390, filed Mar. 5, 1997.

The invention relates to propynyl or dienyl biaromatic compounds as novel and useful industrial products. It also relates to the use of these novel compounds in pharmaceutical compositions intended for use in human or veterinary medicine, or alternatively in cosmetic compositions.

The compounds according to the invention have pronounced activity in the fields of cell differentiation and cell proliferation, and find applications more particularly in the topical and systemic treatment of dermatological complaints associated with a disorder of keratinization, dermatological (or other) complaints with an inflammatory and/or immunoallergic component, and dermal or epidermal proliferations, these being either benign or malignant. These compounds may also be used in the treatment of degenerative diseases of connective tissue, for combating either light-induced or chronological ageing of the skin, and for treating disorders of cicatrization. They moreover find an application in the ophthalmological field, in particular in the treatment of corneopathies.

The compounds according to the invention may also be used in cosmetic compositions for body and hair hygiene.

The compounds according to the invention may be represented by the general formula (I) below:

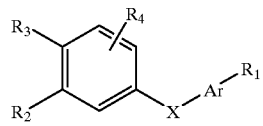

(I)

in which:

$R_1$ represents
  (i) the —$CH_3$ radical
  (ii) the radical —$CH_2$—O—$R_6$
  (iii) the radical —O—$R_6$
  (iv) the radical —CO—$R_7$
$R_6$ and $R_7$ having the meanings given below,
  Ar represents a radical chosen from the radicals of formulae (a)–(e) below:

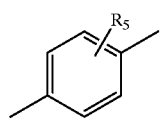

(a)

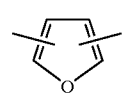

(b)

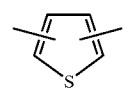

(c)

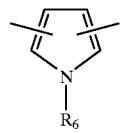

(d)

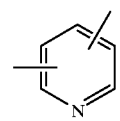

(e)

$R_5$ and $R_6$ having the meanings given below,
X represents a radical of formula:

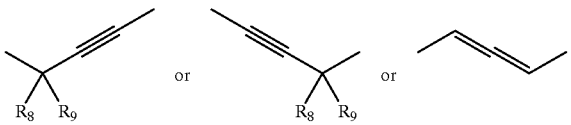

$R_8$ $R_9$ having the meanings given below,
$R_2$ and $R_3$, which may be identical or different, represent
  (i) a hydrogen atom,
  (ii) a linear or branched alkyl radical having from 1 to 20 carbon atoms,
  (iii) a radical —$OR_6$,
  (iv) a radical —$SR_6$,
$R_6$ having the meaning given below,
it being understood that $R_2$ and $R_3$, taken together, may form, with the adjacent aromatic ring, a 5- or 6-membered ring optionally substituted with methyl groups and/or optionally interrupted by an oxygen or sulphur atom,
and it being understood that $R_2$ and $R_3$ cannot simultaneously have the meanings (i), (iii) and (iv) mentioned above,
$R_4$ and $R_5$, which may be identical or different, represent a hydrogen atom, a halogen atom, a linear or branched alkyl radical having from 1 to 20 carbon atoms or a radical —$OR_6$,
it being understood that when $R_4$ is a hydroxyl radical, then $R_2$ and $R_3$ form, with the adjacent aromatic ring, a 5- or 6-membered ring optionally substituted with methyl groups and/or optionally interrupted by an oxygen or sulphur atom,
$R_6$ represents a hydrogen atom, a lower alkyl radical or a radical —$COR_{10}$
$R_{10}$ having the meaning given below,
$R_7$ represents:
  (a) a hydrogen atom
  (b) a lower alkyl radical
  (c) a radical of formula:

R' and R" having the meaning given below,
  (d) a radical —$OR_{11}$,
  (e) a radical —$NHOR_6$,
$R_{11}$ having the meaning given below, R$_8$ and R$_9$, taken separately, either simultaneously have the same meaning: a hydrogen atom or a radical —OR$_{10}$, or one of them represents a hydrogen atom and the other represents a lower alkyl radical, or, taken together, form a ring —Y—(CH$_2$)$_n$—Y—, with Y representing an oxygen or sulphur atom and with n equal to 2 or 3, R$_{10}$ represents a lower alkyl radical, R$_{11}$ represents a hydrogen atom, a linear or branched alkyl radical having from 1 to 20 carbon atoms, an alkenyl radical, a mono- or polyhydroxyalkyl radical, an optionally substituted aryl or aralkyl radical, a sugar residue or an amino acid or peptide residue, R' and R", which may be identical or different, represent a hydrogen atom, a lower alkyl radical, a mono- or polyhydroxyalkyl radical, an optionally substituted aryl radical or an amino acid or sugar residue, or alternatively, taken together, form a heterocycle.

The invention is also directed towards compounds which are intermediates in the synthesis of the compounds of general formula (I), of general formula (II)

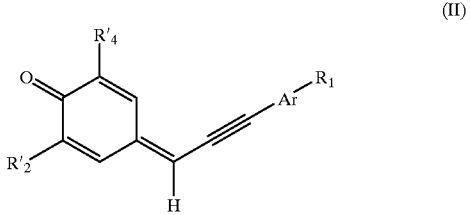

(II)

in which R$_1$ and Ar have the same meanings as for the general formula (I) and R'$_2$ and R'$_4$, which may be identical or different, represent a linear or branched alkyl radical having from 1 to 20 carbon atoms.

The invention is also directed towards the salts of the compounds of formulae (I) and (II) when R$_1$ represents a carboxylic acid function, and the geometrical and optical isomers of the said compounds of formulae (I) and (II).

When the compounds according to the invention are in the form of salts, they are preferably salts of an alkali metal or alkaline earth metal, or alternatively of zinc or of an organic amine.

According to the present invention, the expression lower alkyl radical is understood to refer to a radical having from 1 to 12, preferably from 1 to 9, carbon atoms, advantageously the methyl, ethyl, propyl, isopropyl, butyl, tert-butyl, pentyl, hexyl, heptyl, nonyl, decyl and dodecyl radicals.

The expression linear alkyl radical having from 1 to 20 carbon atoms is understood to refer in particular to the methyl, ethyl, propyl, pentyl, hexyl, octyl, decyl, dodecyl, hexadecyl and octadecyl radicals.

The expression branched alkyl radical having from 1 to 20 carbon atoms is understood to refer in particular to the 2-ethylhexyl, 2-methylbutyl, 2-methylpentyl, 1-methylhexyl and 3-methylheptyl radicals.

Among the monohydroxyalkyl radicals, a radical having 2 or 3 carbon atoms, in particular a 2-hydroxyethyl, 2-hydroxypropyl or 3-hydroxypropyl radical, is preferred.

Among the polyhydroxyalkyl radicals, a radical having from 3 to 6 carbon atoms and from 2 to 5 hydroxyl groups, such as the 2,3-dihydroxypropyl, 2,3,4-trihydroxybutyl and 2,3,4,5-tetrahydroxypentyl radicals or the pentaerythritol residue, is preferred.

Among the aryl radicals, a phenyl radical optionally substituted with at least one halogen atom, a hydroxyl or a nitro function, is preferred.

Among the aralkyl radicals, the benzyl or phenethyl radical optionally substituted with at least one halogen atom, a hydroxyl or a nitro function, is preferred.

Among the alkenyl radicals, a radical containing from 2 to 5 carbon atoms and having one or more ethylenic unsaturations, in particular such as the allyl radical, is preferred.

The term sugar residue is understood to refer to a residue derived in particular from glucose, galactose or mannose, or alternatively from glucuronic acid.

The term amino acid residue is understood to refer in particular to a residue derived from lysine, glycine or aspartic acid, and the term peptide residue is understood to refer more particularly to a dipeptide or tripeptide residue resulting from the combination of amino acids.

Lastly, the term heterocycle is understood to refer preferably to a piperidino, morpholino, pyrrolidino or piperazino radical, optionally substituted in position 4 with a C$_1$–C$_6$ alkyl or mono- or polyhydroxyalkyl radical as defined above.

When the radicals R$_4$ and R$_5$ represent a halogen atom, this is preferably a fluorine, bromine or chlorine atom.

Among the compounds of formula (I) above which fall within the scope of the present invention, mention may be made in particular of the following compounds:

4-[3-(3,5-Di-tert-butyl-4-hydroxyphenyl)-1-propynyl]benzoic acid.

2-Hydroxy-4-[3-(3,5-di-tert-butyl-4-hydroxyphenyl)-1-propynyl]benzoic acid.

4-[3-(5,6,7,8-Tetrahydro-5,5,8,8-tetramethyl-2-naphthyl)-1-propynyl]benzoic acid.

Methyl 2-hydroxy-4-[3-(5,6,7,8-tetrahydro-5,5,8,8-tetramethyl-2-naphthyl)-1-propynyl]benzoate.

2-Hydroxy-4-[3-(5,6,7,8-tetrahydro-5,5,8,8-tetramethyl-2-naphthyl)-1-propynyl]benzoic acid.

2-Hydroxy-4-[3-(3-hydroxy-5,6,7,8-tetrahydro-5,5,8,8-tetramethyl-2-naphthyl)-1-propynyl]benzoic acid.

2-Hydroxy-4-[3-(5,6,7,8-tetrahydro-5,5,8,8-tetramethyl-2-naphthyl)-1-propynyl]benzenemethanol.

Diethanolamine 2-hydroxy-4-[3-(5,6,7,8-tetrahydro-5,5,8,8-tetramethyl-2-naphthyl)-1-propynyl]benzoate.

Lithium 2-hydroxy-4-[3-(5,6,7,8-tetrahydro-5,5,8,8-tetramethyl-2-naphthyl)-1-propynyl]benzoate.

4-[3-(5,6,7,8-Tetrahydro-5,5,8,8-tetramethyl-2-naphthyl)-2-propynyl]benzoic acid.

2-Hydroxy-4-[3-(4,4-dimethylthiochroman-6-yl)-1-propynyl]benzoic acid.

2-Hydroxy-4-[3-(8,8-dimethyl-5,6,7,8-tetrahydro-2-naphthyl)-1-propynyl]benzoic acid.

2-Hydroxy-4-[3-(5,5-dimethyl-5,6,7,8-tetrahydro-2-naphthyl)-1-propynyl]benzoic acid.

Ethyl 4-[3-(5,6,7,8-tetrahydro-5,5,8,8-tetramethyl-2-naphthyl)-1-propynyl]benzoate.

4-[3-(5,6,7,8-Tetrahydro-5,5,8,8-tetramethyl-2-naphthyl)-1-propynyl]benzamide.

N-Ethyl-4-[3-(5,6,7,8-tetrahydro-5,5,8,8-tetramethyl-2-naphthyl)-1-propynyl]benzamide.

4-[3-(5,6,7,8-Tetrahydro-5,5,8,8-tetramethyl-2-naphthyl)-1-propynyl]benzoic acid morpholide.

N-(4-Hydroxyphenyl)-4-[3-(5,6,7,8-tetrahydro-5,5,8,8-tetramethyl-2-naphthyl)-1-propynyl]benzamide.

4-[3-(5,6,7,8-Tetrahydro-5,5,8,8-tetramethyl-2-naphthyl)-1-propynyl]benzaldehyde.

4-[3-(5,6,7,8-Tetrahydro-5,5,8,8-tetramethyl-2-naphthyl)-1-propynyl]phenol.

[3-(5,6,7,8-Tetrahydro-5,5,8,8-tetramethyl-2-naphthyl)-1-propynyl]benzenemethanol.

4-[3-(5,6,7,8-Tetrahydro-5,5,8,8-tetramethyl-2-naphthyl)-1-propynyl]toluene.

Hexyl 4-[3-(5,6,7,8-tetrahydro-5,5,8,8-tetramethyl-2-naphthyl)-1-propynyl]benzoate.

N-Hydroxy-4-[3-(5,6,7,8-tetrahydro-5,5,8,8-tetramethyl-2-naphthyl)-1-propynyl]benzamide.

N-Hydroxy-2-hydroxy-4-[3-(5,6,7,8-tetrahydro-5,5,8,8-tetramethyl-2-naphthyl)-1-propynyl]benazamide.

2-Methyl-4-[3-(5,6,7,8-tetrahydro-5,5,8,8-tetramethyl-2-naphthyl)-1-propynyl]benzoic acid.

3-Methyl-4-[3-(5,6,7,8-tetrahydro-5,5,8,8-tetramethyl-2-naphthyl)-1-propynyl]benzoic acid.

6-[3-(5,5,8,8-Tetramethyl-5,6,7,8-tetrahydro-2-naphthyl)propa-1,2-dienyl]nicotinic acid.

4-[3-(5,5,8,8-Tetramethyl-5,6,7,8-tetrahydro-2-naphthyl)propa-1,2-dienyl]benzoic acid.

2-Hydroxy-4-[3-(5,5,8,8-tetramethyl-5,6,7,8-tetrahydro-2-naphthyl)propa-1,2-dienyl]benzoic acid.

2-Hydroxy-4-[3-(5,6,7,8-tetrahydro-5,5,8,8-tetramethyl-2-naphthyl)-1-butynyl]benzoic acid.

5-[3-(5,6,7,8-Tetrahydro-5,5,8,8-tetramethyl-2-naphthyl)-1-propynyl]-2-pyridinecarboxylic acid.

4-[3-(3,5,5,8,8-Pentamethyl-5,6,7,8-tetrahydro-2-naphthyl)-1-propynyl]benzoic acid.

2-[3-(5,6,7,8-Tetrahydro-5,5,8,8-tetramethyl-2-naphthyl)-1-propynyl]-4-thiophenecarboxylic acid.

2-[3-(3,5,5,8,8-Pentamethyl-5,6,7,8-tetrahydro-2-naphthyl)-1-propynyl]-4-thiophenecarboxylic acid.

2-Hydroxy-4-[3-(3-tert-butyl-4-methoxyphenyl)-1-propynyl]benzoic acid.

2-Hydroxy-4-[3-(3-tert-butyl-4-hydroxyphenyl)-1-propynyl]benzoic acid.

Among the compounds of formula (II) above which fall within the scope of the present invention, mention may be made in particular of the following compounds:

4-[3-(3,5-Di-tert-butyl-4-oxo-2,5-cyclohexadien-1-ylidene)-1-propynyl]benzoic acid.

2-Hydroxy-4-[3-(3,5-Di-tert-butyl-4-oxo-2,5-cyclohexadien-1-ylidene)-1-propynyl]benzoic acid.

According to the present invention, the compounds of formula (I) or (II) more particularly preferred are those for which at least one, and preferably all, of the following conditions is/are satisfied:

—$R_1$ represents the radical —CO—$R_7$,

Ar represents the radicals of formula (a) or (e).

More particularly, the preferred compounds of formula (I) are those for which $R_8$ and $R_9$, taken separately, either represent hydrogen atoms or one of them represents a hydrogen atom and the other represents a lower alkyl radical. Even more preferably, $R_8$ and $R_9$ represent hydrogen atoms.

Figure 2:
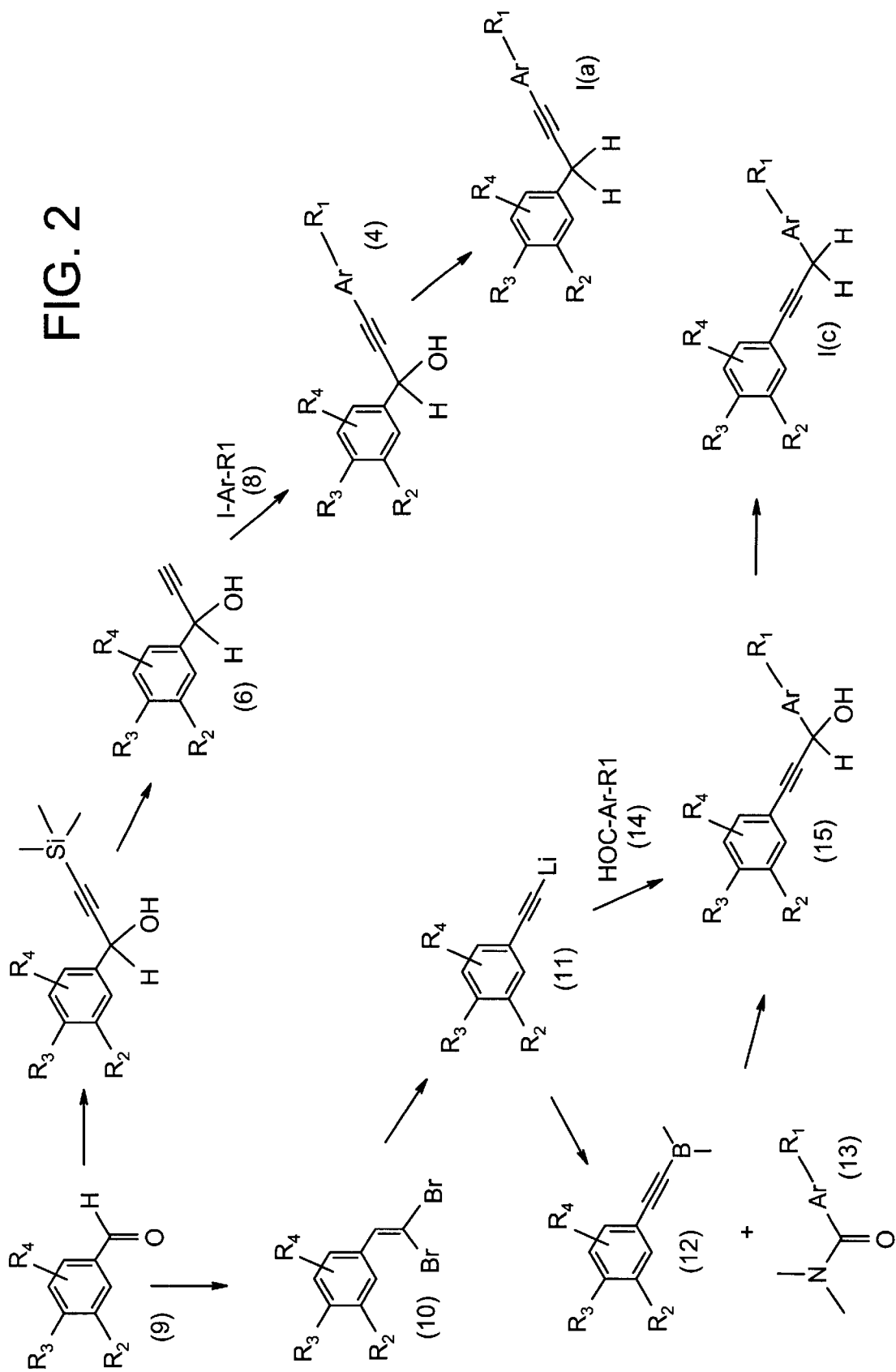
Figure 3:
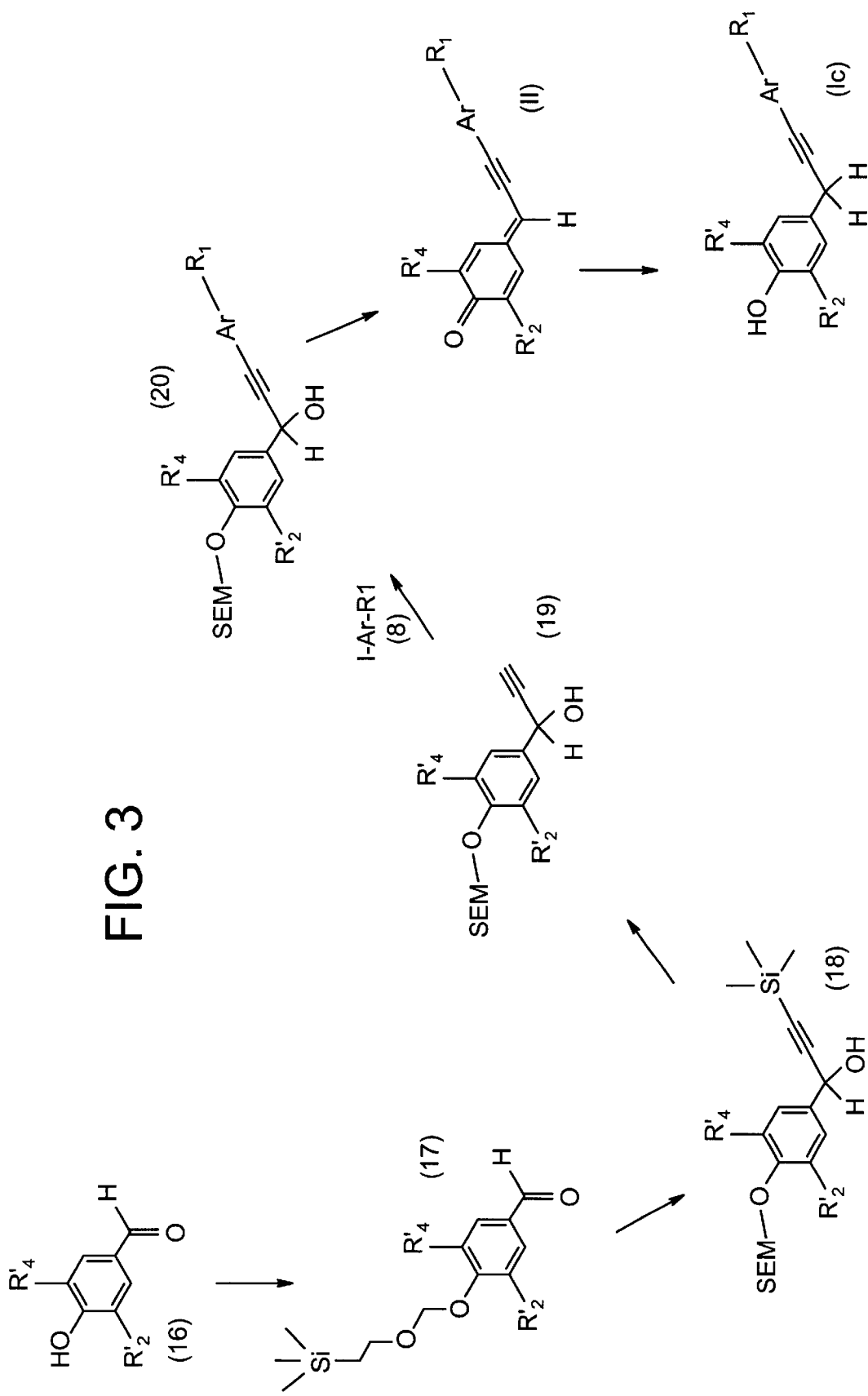

The subject of the present invention is also processes for the preparation of the compounds of formulae (I) and (II) above according to the reaction schemes given in FIGS. 1, 2 and 3.

Thus, the derivatives of formula (Ia) may be prepared (FIG. 1) by a reaction sequence comprising the action of a benzoyl chloride of formula (1) with an acetylenic derivative of formula (2) in the presence of a Lewis acid (for example $AlCl_3$) in a chlorinated solvent, such as dichloromethane. The ketone (3) thus obtained is reduced to alcohol (4) by the action of an alkali metal hydride, such as sodium borohydride, in an alcoholic solvent (for example methanol). Reduction of the alcohol function to carbide may be carried out in the presence of trimethylsilyl iodide in a solvent such as hexane or by hydride transfer from a silane, such as triethylsilane, in the presence of $BF_3.Et_2O$ in a chlorinated solvent such as methylene chloride.

The derivatives of formula (Ia) may also be prepared (FIG. 1) by a reaction sequence comprising the action of a benzoyl chloride of formula (1) with lithium trimethylacetylenide in the presence of a Lewis acid (for example $AlCl_3$) in a chlorinated solvent such as dichloromethane. The ketone (5) thus obtained is first reduced to alcohol (6) by the action of an alkali metal hydride, such as sodium borohydride, in an alcoholic solvent (for example methanol), and then to carbide (7), for example by hydride transfer from a silane such as triethylsilane, in the presence of $BF_3.Et_2O$ in a chlorinated solvent such as methylene chloride. Next, the compound (7) is coupled with a halogenated derivative (8) preferably an iodo or bromo derivative, in the presence of a palladium catalyst [for example bis(triphenylphosphine)palladium(II) chloride] in a solvent such as triethylamine.

The compounds of formula (Ib) may be obtained (FIG. 1) from the ketone derivative (3) by reaction with a glycol (ethylene glycol or propylene glycol) or a dithiol (ethanedithiol, propanedithiol) in the presence of pyridinium para-toluenesulphonate in an aromatic solvent such as toluene, with azeotropic entrainment of the water formed.

The compounds of formula (Ia) may also be prepared (FIG. 2) by a reaction sequence comprising the action of lithium trimethylsilylacetylenide with the aldehyde compounds (9) and deprotection with tetrabutylammonium fluoride in THF and production of the propargyl alcohol (6). Next, coupling is carried out with a halo derivative (8), preferably an iodo or bromo derivative, in the presence of a palladium catalyst [for example bis(triphenylphosphine) palladium(II) chloride] in a solvent such as triethylamine, and reduction of the alcohol function to carbide, as above.

The compounds of formula (Ic) may be prepared (FIG. 2) from propargyl alcohol derivatives (15) by reduction of the alcohol function to carbide as above, the propargyl alcohol derivatives (15) being prepared:

either by the action of a boron acetylenide (12) (prepared in situ from lithium phenylacetylenide (11) and boron trifluoride at −78° C. in THF) with a tertiary benzamide of formula (13) in an organic solvent, such as THF, or by the action of lithium phenylacetylenide (11) on the aldehyde derivatives (14).

The compounds of formula (Ic) may be prepared (FIG. 3) from the compounds of formula (II) by the action of an alkali metal hydride, such as sodium borohydride, in an alcoholic solvent (for example methanol). The compounds of formula (II) are prepared by a sequence of reactions from hydroxybenzaldehyde compounds (16), comprising protection of the phenol function by the action of 2-(trimethylsilyl)ethoxymethyl chloride (SEMCl) (17), followed by the action of lithium trimethylsilylacetylenide (18) and selective deprotection of the trimethylsilyl group borne by the acetylenic derivative with tetrabutylammonium fluoride in THF and production of the propargyl alcohol (19). By coupling with a halo derivative (8), preferably an iodo or bromo derivative, in the presence of a palladium catalyst [for example bis(triphenylphosphine)palladium(II) chloride] in a solvent, such as triethylamine, the compound (20) is obtained. Cleavage of the protecting group (SEM) is carried out with trifluoroacetic acid in a chlorinated solvent, such as methylene chloride.

The subject of the present invention is also, as medicinal product, the compounds of formulae (I) and (II) as defined above.

These compounds are active in the test of differentiation of mouse embryonic teratocarcinoma cells (F9) (Cancer Research 43, p. 5258, 1983) and/or in the test of inhibition of ornithine decarboxylase after induction with TPA in mice (Cancer Research 38, pp. 793–801, 1978). These tests show the activities of the compounds in the fields of cell differentiation and cell proliferation respectively.

These compounds also have very advantageous kinetic parameters for the pharmaceutical field when compared with other synthetic compounds of retinoid type (the half-life for removal and the average residence time of these compounds in the body are low).

The compounds of formula (I) or (II) according to the invention are particularly suitable in the following fields of treatment:

1) for treating dermatological complaints associated with a keratinization disorder which has a bearing on differentiation and on proliferation, in particular for treating common acne, comedones, polymorphonuclear leukocytes, acne rosacea, nodulocystic acne, acne conglobata, senile acne and secondary acnes such as solar, medication-related or occupational acne,
2) for treating other types of keratinization disorder, in particular ichthyosis, ichthyosiform states, Darier's disease, palmoplantar keratoderma, leucoplasias and leucoplasiform states, and cutaneous or mucous (buccal) lichen,
3) for treating other dermatological complaints associated with a keratinization disorder with an inflammatory and/or immunoallergic component and, in particular, all forms of psoriasis, whether it is cutaneous, mucous or ungual psoriasis and even psoriatic rheumatism, or alternatively cutaneous atopy, such as eczema or respiratory atopy or alternatively gingival hypertrophy; the compounds may also be used in certain inflammatory complaints which do not exhibit a disorder of keratinization,
4) for treating all dermal or epidermal proliferations, whether benign or malignant and whether they are of viral origin or otherwise, such as common warts, flat warts and verruciform epidermodysplasia, it being also possible for the oral or florid papillomatoses and the proliferations to be induced by ultraviolet radiation, in particular in the case of basocellular and spinocellular epithelioma,
5) for treating other dermatological disorders such as bullosis and collagen diseases,
6) for treating certain ophthalmological disorders, in particular corneopathies,
7) for repairing or combating ageing of the skin, whether this is light-induced or chronological ageing, or for reducing actinic keratoses and pigmentations, or any pathologies associated with chronological or actinic ageing,
8) for preventing or curing the stigmata of epidermal and/or dermal atrophy induced by local or systemic corticosteroids, or any other form of cutaneous atrophy,
9) for preventing or treating cicatrization disorders or for preventing or repairing vibices,
10) for combating disorders of sebaceous functioning such as the hyperseborrhoea of acne or simple seborrhoea,
11) in the treatment or prevention of cancerous or pre-cancerous states,
12) in the treatment of inflammatory complaints such as arthritis,
13) in the treatment of any general or skin complaint of viral origin, such as Kaposi's syndrome,
14) in the prevention or treatment of alopecia,
15) in the treatment of dermatological or general complaints having an immunological component,
16) in the treatment of complaints of the cardiovascular system such as arteriosclerosis, or hypertension, as well as insulin-independent diabetes,
17) in the treatment of skin disorders due to exposure to UV radiation.

In the therapeutic fields mentioned above, the compounds according to the invention may advantageously be employed in combination with other compounds having retinoid-type activity, with D vitamins or derivatives thereof, with corticosteroids, with anti-free-radical agents, α-hydroxy or α-keto acids or derivatives thereof, or alternatively with ion-channel blockers. The expression D vitamins or derivatives thereof is understood to refer, for example, to derivatives of vitamin $D_2$ or $D_3$ and in particular 1,25-dihydroxyvitamin $D_3$. The expression anti-free-radical agents is understood to refer, for example, to α-tocopherol, superoxide dismutase, ubiquinol or certain metal-chelating agents. The expression α-hydroxy or α-keto acids or derivatives thereof is understood to refer, for example, to lactic acid, malic acid, citric acid, glycolic acid, mandelic acid, tartaric acid, glyceric acid or ascorbic acid or salts, amides or esters thereof. Lastly, the expression ion-channel blockers is understood to refer, for example, to Minoxidil (2,4-diamino-6-piperidinopyrimidine 3-oxide) and derivatives thereof.

The subject of the present invention is also medicinal compositions containing at least one compound of formula (I) or (II) as defined above, one of the optical or geometric isomers thereof or one of the salts thereof.

The subject of the present invention is thus a novel medicinal composition intended in particular for treating the abovementioned complaints, and which is characterized in that it comprises, in a pharmaceutically acceptable support which is compatible with the mode of administration selected for this composition, at least one compound of formula (I) or (II), one of the optical or geometric isomers thereof or one of the salts thereof.

The compounds according to the invention may be administered enterally, parenterally, topically or ocularly.

Via the enteral route, the medicinal products may be in the form of tablets, gelatin capsules, sugar-coated tablets, syrups, suspensions, solutions, powders, granules, emulsions, microspheres or nanospheres or polymeric or lipid vesicles which allow controlled release. Via the parenteral route, the compositions may be in the form of solutions or suspensions for infusion or for injection.

The compounds according to the invention are generally administered at a daily dose of about 0.01 mg/kg to 100 mg/kg of body weight, taken in 1 to 3 doses.

Via the topical route, the pharmaceutical compositions based on compounds according to the invention are more particularly intended for treating the skin and mucous membranes and may, in this case, be in the form of ointments, creams, milks, salves, powders, impregnated pads, solutions, gels, sprays, lotions or suspensions. They may also be in the form of microspheres or nanospheres or polymeric or lipid vesicles or polymeric patches and hydrogels which allow controlled release. These topical-route compositions may moreover be either in anhydrous form or in an aqueous form, depending on the clinical indication.

Via the ocular route, they are mainly eyedrops.

These compositions for topical or ocular use contain at least one compound of formula (I) or (II) as defined above, or one of the optical or geometric isomers thereof, or alternatively one of the salts thereof, at a concentration preferably of between 0.001% and 5% by weight relative to the total weight of the composition.

The compounds of formula (I) or (II) according to the invention also find an application in the cosmetic field, in particular in body and hair hygiene and especially for treating skin-types with a tendency towards acne, for promoting the regrowth of the hair, for combating hair loss, for controlling the greasy appearance of the skin or the hair, in protection against the harmful effects of sunlight or in the treatment of physiologically dry skin-types, and for preventing and/or combating light-induced or chronological ageing.

In the cosmetic field, the compounds according to the invention may also advantageously be employed in combination with other compounds having retinoid-type activity, with D vitamins or derivatives thereof, with corticosteroids, with anti-free-radical agents, $\alpha$-hydroxy or $\alpha$-keto acids or derivatives thereof, or alternatively with ion-channel blockers, all of these different products being as defined above.

The present invention is thus also directed towards a cosmetic composition which is characterized in that it comprises, in a cosmetically acceptable support which is suitable for topical application, at least one compound of formula (I) or (II) as defined above, or one of the optical or geometric isomers thereof or one of the salts thereof, it being possible for this cosmetic composition to be in the form of a cream, a milk, a lotion, a gel, microspheres or nanospheres or polymeric or lipid vesicles, a soap or a shampoo.

The concentration of compound of formula (I) or (II) in the cosmetic compositions according to the invention is advantageously between 0.001% and 3% by weight relative to the composition as a whole.

The medicinal and cosmetic compositions according to the invention may also contain inert additives or even pharmacodynamically or cosmetically active additives or combinations of these additives and, in particular, wetting agents; depigmenting agents such as hydroquinone, azelaic acid, caffeic acid or kojic acid; emollients; moisturizing agents such as glycerol, PEG 400, thiamorpholinone and derivatives thereof, or alternatively urea; anti-seborrhoea or anti-acne agents such as S-carboxymethylcysteine, S-benzylcysteamine, the salts and the derivatives thereof, or benzoyl peroxide; antibiotics such as erythromycin and esters thereof, neomycin, clindamycin and esters thereof, and tetracyclines; antifungal agents such as ketoconazole or 4,5-polymethylene-3-isothiazolidones; agents for promoting the regrowth of the hair, such as minoxidil (2,4-diamino-6-piperidinopyrimidine 3-oxide) and derivatives thereof, diazoxide (7-chloro-3-methyl-1,2,4-benzothiadiazine 1,1-dioxide) and phenytoin (5,4-diphenylimidazolidine-2,4-dione); non-steroidal anti-inflammatory agents; carotenoids and, in particular, $\beta$-carotene; anti-psoriatic agents such as anthraline and derivatives thereof and, lastly, eicosa-5,8,11, 14-tetraynoic acid and eicosa-5,8,11-triynoic acid, the esters and the amides thereof.

The compositions according to the invention may also contain flavour-enhancing agents, preserving agents such as para-hydroxybenzoic acid esters, stabilizing agents, moisture regulators, pH regulators, osmotic pressure modifiers, emulsifying agents, UV-A and UV-B screening agents, and antioxidants such as $\alpha$-tocopherol, butylhydroxyanisole or butylhydroxytoluene.

Several examples of the production of active compounds of formula (I) or (II) according to the invention, as well as various solid formulations based on such compounds, will now be given by way of illustration and with no limitation. Hereinabove and hereinbelow the percentages given are by weight unless indicated otherwise.

EXAMPLE 1

4-[3-(3,5-Di-tert-butyl-4-oxo-2,5-cyclohexadien-1-ylidene)-1-propynyl]benzoic acid (a) 3,5-Di-tert-butyl-4-(2-trimethylsilylethoxymethoxy) benzaldehyde 12.3 g (52 mmol) of 3,5-di-tert-butyl-4-hydroxybenzaldehyde and 100 ml of THF are introduced into a round-bottomed flask. 10 ml (58 mmol) of diisopropylethylamine and 10.3 ml (58 mmol) of 2-trimethylsilylethoxymethane chloride are added successively and the mixture is refluxed for three hours. The reaction medium is poured into water and extracted with ethyl ether, and the organic phase is separated out after settling has taken place, dried over magnesium sulphate and evaporated. The residue obtained is purified by chromatography on a column of silica eluted with a mixture of ethyl acetate and hexane (3/97% by volume). After evaporation of the solvents, 15.6 g (82%) of the expected product are collected in the form of a colourless oil.

(b) $\alpha$-Trimethylsilylethynyl-3,5-di-tert-butyl-4-(2-trimethylsilylethoxymethoxy)benzenemethanol 6.6 ml (46.5 mmol) of trimethylsilylacetylene and 50 ml of THF are introduced into a three-necked flask. A solution of 18.6 ml (46.5 mmol) of n-butyllithium (2.5 M in hexane) is added dropwise at −78° C. and under a stream of nitrogen, and the mixture is allowed to return to room temperature.

This solution is introduced dropwise into a solution of 15.4 g (42.3 mmol) of 3,5-di-tert-butyl-4-(2-trimethylsilylethoxymethoxy)benzaldehyde in 50 ml of THF at −78° C. The reaction medium is allowed to return to room temperature, poured into aqueous ammonium chloride solution and extracted with ethyl ether and the organic phase is separated out after settling has taken place, dried over magnesium sulphate and evaporated. 18.5 g (95%) of the expected alcohol are obtained in the form of a yellow oil.

(c) $\alpha$-Ethynyl-3,5-di-tert-butyl-4-(2-trimethylsilylethoxymethoxy)benzenemethanol 18.5 g (40 mmol) of $\alpha$-trimethylsilylethynyl-3,5-di-tert-butyl-4-(2-trimethylsilylethoxymethoxy)benzenemethanol and 50 ml of THF are introduced into a round-bottomed flask and 40 ml (44 mmol) of tetrabutylammonium fluoride solution (1.1 M in THF) are added dropwise. The mixture is stirred at room temperature for one hour, the reaction medium is poured into water and extracted with ethyl ether and the organic phase is separated out after settling has taken place, dried over magnesium sulphate and evaporated. The residue obtained is purified by chromatography on a column of silica eluted with a mixture of ethyl acetate and hexane (5/95 by volume). After evaporation of the solvents, 13.5 g (86%) of $\alpha$-ethynyl-3,5-di-tert-butyl-4-(2-trimethylsilylethoxymethoxy)benzenemethanol are collected in the form of a colourless oil.

(d) Methyl 4-{3-hydroxy-3-[3,5-di-tert-butyl-4-(2-trimethylsilylethoxymethoxy)phenyl]-1-propynyl}benzoate 6 g (15.4 mmol) of $\alpha$-ethynyl-3,5-di-tert-butyl-4-(2-trimethylsilylethoxymethoxy)benzenemethanol, 4.1 g (15.4 mmol) of methyl 4-iodobenzoate and 50 ml of triethylamine are introduced into a three-necked flask. The reaction medium is degassed with nitrogen for 30 minutes and 820 mg (1.2 mmol) of bis(triphenylphosphine)palladium(II) chloride and 360 mg (1.9 mmol) of copper iodide are then added successively. The reaction medium is stirred at room temperature for four hours and evaporated to dryness, and the residue obtained is taken up in water and ethyl ether. The organic phase is separated out after settling has taken place, dried over magnesium sulphate and then evaporated. The residue obtained is purified by chromatography on a column of silica eluted with a mixture of dichloromethane and heptane (80/20% by volume); 6.7 g (84%) of methyl 4-{3-hydroxy-3-[3,5-di-tert-butyl-4-(2-trimethylsilylethoxymethoxy)phenyl]-1-propynyl}benzoate are collected, with a melting point of 91–2° C.

(e) 4-{3-Hydroxy-3-[3,5-di-tert-butyl-4-(2-trimethylsilylethoxymethoxy)phenyl]-1-propynyl}benzoic acid 2.4 g (4.6 mmol) of the above ester, 8.4.g (200 mmol) of lithium hydroxide and 100 ml of THF are introduced into a round-bottomed flask. The reaction medium is refluxed for 18 hours and evaporated to dryness. The residue is taken up in water, acidified to pH 1 and extracted with ethyl ether and the organic phase is separated out after settling has taken place, dried over magnesium sulphate and evaporated. The residue is triturated from heptane and filtered and 2.2 g (94%) of the expected acid are collected, with a melting point of 155–6° C.

(f) 4-[3-(3,5-Di-tert-butyl-4-oxo-2,5-cyclohexadien-1-ylidene)-1-propynyl]benzoic acid 2.2 g (4.7 mmol) of 4-{3-Hydroxy-3-[3,5-di-tert-butyl-4-(2-trimethylsilylethoxymethoxy)phenyl]-1-propynyl}benzoic acid and 75 ml of dichloromethane are introduced into a three-necked flask. 360 µl (4.7 mmol) of trifluoroacetic acid are added at −78° C. and the mixture is allowed to return to room temperature. The reaction medium is poured into water and extracted with ethyl ether, and the organic phase is separated out after settling has taken place, dried over magnesium sulphate and evaporated. The residue obtained is triturated from heptane, filtered and then dried. 1.6 g (90%) of 4-[3-(3,5-di-tert-butyl-4-oxo-2,5-cyclohexadien-1-ylidene)-1-propynyl]benzoic acid are collected, with a melting point of 216–8° C.

EXAMPLE 2

4-[3-(3,5-Di-tert-butyl-4-hydroxyphenyl)- 1-propynyl]benzoic acid 756 mg (2 mmol) of 4-[3-(3,5-di-tert-butyl-4-oxo-2,5-cyclohexadien-1-ylidene)-1-propynyl]benzoic acid and 50 ml of a mixture (50/50) of THF and methanol are introduced into a three-necked flask. 152 mg (4 mmol) of sodium borohydride are added at 0° C. and the mixture is allowed to return to room temperature. The reaction medium is poured into water and extracted with ethyl ether, and the organic phase is separated out after settling has taken place, dried over magnesium sulphate and evaporated. The residue obtained is triturated from refluxing heptane, filtered and dried. 510 mg (64%) of 4-[3-(3,5-Di-tert-butyl-4-hydroxyphenyl)-1-propynyl]benzoic acid are collected, with a melting point of 198–9° C.

EXAMPLE 3

2-Hydroxy-4-[3-(3,5-di-tert-butyl-4-oxo-2,5-cyclohexadien-1-ylidene)-1-propynyl]benzoic acid (a) Methyl 2-hydroxy-4-{3-hydroxy-3-[3,5-di-tert-butyl-4-(2-trimethylsilylethoxymethoxy)phenyl]-1-propynyl}benzoate In a similar manner to Example 1(d), by reaction of 6.7 g (17.3 mmol) of α-ethynyl-3,5-di-tert-butyl-4-(2-trimethylsilylethoxymethoxy)benzenemethanol with 4.8 g (17.3 mmol) of methyl 2-hydroxy-4-iodobenzoate, 8.5 g (91%) of the expected ester are obtained in the form of a yellow oil.

(b) 2-Hydroxy-4-{3-hydroxy-3-[3,5-di-tert-butyl-4-(2-trimethylsilylethoxymethoxy)phenyl]-1-propynyl}benzoic acid In a similar manner to Example 1(e), starting with 8.4 g (15.5 mmol) of methyl 2-hydroxy-4-{3-hydroxy-3-[3,5-di-tert-butyl-4-(2-trimethylsilylethoxymethoxy)phenyl]-1-propynyl}benzoate, 7.4 g (91%) of the expected acid are obtained, with a melting point of 146–7° C.

(c) 2-Hydroxy-4-[3-(3,5-di-tert-butyl-4-oxo-2,5-cyclohexadien-1-ylidene)-1-propynyl]benzoic acid In a similar manner to Example 1(f), starting with 2.6 g (5 mmol) of 2-hydroxy-4-{3-hydroxy-3-[3,5-di-tert-butyl-4-(2-trimethylsilylethoxymethoxy)phenyl]-1-propynyl}benzoic acid, 1.7 g (89%) of 2-hydroxy-4-[3-(3,5-di-tert-butyl-4-oxo-2,5-cyclohexadien-1-ylidene)-1-propynyl]benzoic acid are obtained, with a melting point of 203° C. with decomposition.

EXAMPLE 4

2-Hydroxy-4-[3-(3,5-di-tert-butyl-4-hydroxyphenyl)-1-propynyl]benzoic acid

In a similar manner to Example 2, starting with 1 g (2.6 mmol) of 2-hydroxy-4-[3-(3,5-di-tert-butyl-4-oxo-2,5-cyclohexadien-1-ylidene)-1-propynyl]benzoic acid, 510 mg (51%) of 2-hydroxy-4-[3-(3,5-di-tert-butyl-4-hydroxyphenyl)-1-propynyl]benzoic acid are obtained, with a melting point of 205–6° C.

EXAMPLE 5

4-[3-(5,6,7,8-Tetrahydro-5,5,8,8-tetramethyl- 2-naphthyl)-1-propynyl]benzoic acid (a) Methyl 4-trimethylsilylethynylbenzoate 21.5 g (0.1 mol) of methyl 4-bromobenzoate, 300 ml of triethylamine and a mixture of 200 mg of palladium acetate and 400 mg of triphenylphosphine are introduced into a three-necked flask under a stream of nitrogen. 20 g (0.20 mol) of trimethylsilylacetylene are then added, the mixture is heated gradually to 90° C. over 1 hour and left at this temperature for 5 hours. The reaction medium is cooled, the salt is filtered off and the filtrate is evaporated. The residue is taken up in 200 ml of hydrochloric acid (5%) and 400 ml of ethyl ether. The ether phase is separated out after settling has taken place, washed with water, dried over magnesium sulphate and evaporated. The residue obtained is purified by chromatography on a column of silica eluted with dichloromethane. After evaporation of the solvents, 23 g (100%) of the expected derivative are collected in the form of a colourless oil.

(b) Methyl 4-[3-oxo-3-(5,6,7,8-tetrahydro-5,5,8,8-tetramethyl-2-naphthyl)-1-propynyl]benzoate 8.4 g (36 mmol) of 5,6,7,8-tetrahydro-5,5,8,8-tetramethyl-2-naphthoyl chloride, 6.9 g (29.7 mmol) of methyl 4-trimethylsilylethynylbenzoate and 100 ml of dichloromethane are introduced into a round-bottomed flask. 16.8 g (125 mmol) of $AlCl_3$ are added portionwise at 0° C. and the mixture is stirred at room temperature for 8 hours. The reaction medium is poured into ice and extracted with dichloromethane, and the organic phase is separated out after settling has taken place, dried over magnesium sulphate and evaporated. The residue obtained is purified by chromatography on a column of silica eluted with a mixture of dichloromethane and hexane (50/50% by volume). 6.8 g (61%) of the expected product are collected, with a melting point of 113–4° C.

(c) Methyl 4-[3-hydroxy-3-(5,6,7,8-tetrahydro-5,5,8,8-tetramethyl-2-naphthyl)-1-propynyl]benzoate 4.7 g (125 mmol) of the product obtained above and 100 ml of methanol are introduced into a round-bottomed flask.

5.7 g (150 mmol) of CeCl$_3$.7H$_2$O and 530 mg (125 mmol) of sodium borohydride are successively added, while cooling to 0° C., and the mixture is stirred at room temperature for 4 hours. The reaction medium is poured into a water/ethyl ether mixture and the organic phase is separated out after settling has taken place, washed with water, dried over magnesium sulphate and evaporated. The residue obtained is triturated from 100 ml of hexane, filtered and dried. 4 g (85%) of the expected product are collected, with a melting point of 142–3° C.

(d) 4-[3-Hydroxy-3-(5,6,7,8-tetrahydro-5,5,8,8-tetramethyl-2-naphthyl)-1-propynyl]benzoic acid In a similar manner to Example 1(e), starting with 1.7 g (4.5 mmol) of the above methyl ester, 1.3 g (79%) of 4-[3-hydroxy-3-(5,6,7,8-tetrahydro-5,5,8,8-tetramethyl-2-naphthyl)-1-propynyl]benzoic acid are obtained, with a melting point of 146–7° C.

(e) 4-[3-(5,6,7,8-Tetrahydro-5,5,8,8-tetramethyl-2-naphthyl)-1-propynyl]benzoic acid 2.1 ml (8.1 mmol) of BF$_3$.Et$_2$O (48%) and 50 ml of dichloromethane are introduced into a three-necked flask under a stream of nitrogen. 2.6 ml (16.2 mmol) of triethylsilane are added at –20° C., followed by a solution of 1 g (2.7 mmol) of 4-[3-hydroxy-3-(5,6,7,8-tetrahydro-5,5,8,8-tetramethyl-2-naphthyl)-1-propynyl]benzoic acid in 30 ml of dichloromethane and the mixture is stirred at room temperature for 30 minutes. The reaction medium is poured into water and extracted with ethyl ether, and the organic phase is separated out after settling has taken place, dried over magnesium sulphate and evaporated. The residue obtained is purified on a column of silica eluted with dichloromethane. After evaporation of the solvents, 780 mg (82%) of 4-[3-(5,6,7,8-tetrahydro-5,5,8,8-tetramethyl-2-naphthyl)-1-propynyl]benzoic acid are collected, with a melting point of 167–8° C.

EXAMPLE 6

Methyl 2-hydroxy-4-[3-(5,6,7,8-tetrahydro-5,5,8,8-tetramethyl-2-naphthyl)-1propynyl]benzoate (a) α-Trimethylsilylethynyl-(5,6,7,8-tetrahydro-5,5,8,8-tetramethyl-2-naphthalene)methanol 17.13 ml (0.121 mol) of trimethylsilylacetylene and 100 ml of THF are introduced into a three-necked flask. A solution of 48.5 ml (0.121 mol) of n-butyllithium (2.5 M in hexane) is added dropwise at –78° C. under a stream of nitrogen and the mixture is allowed to return to room temperature.

This solution is introduced dropwise into a solution of 23.8 g (0.11 mol) of 5,6,7,8-tetrahydro-5,5,8,8-tetramethyl-2-naphthalenecarboxaldehyde in 100 ml of THF at –78° C. The reaction medium is allowed to return to room temperature, poured into aqueous ammonium chloride solution and extracted with ethyl ether, and the organic phase is separated out after settling has taken place, dried over magnesium sulphate and evaporated. The residue obtained is purified by chromatography on a column of silica eluted with a mixture of dichloromethane and hexane (50/50% by volume). After evaporation of the solvents, 29.9 g (86%) of the expected alcohol are collected in the form of a yellow oil.

(b) α-Ethynyl-5,6,7,8-tetrahydro-5,5,8,8-tetramethyl-2-naphthalene)methanol 29.9 g (95.2 mmol) of α-trimethylsilylethynyl-(5,6,7,8-tetrahydro-5,5,8,8-tetramethyl-2-naphthalene)methanol and 100 ml of THF are introduced into a round-bottomed flask and 103.8 ml (114.2 mmol) of tetrabutylammonium fluoride solution (1.1 M in THF) are added dropwise. The reaction medium is stirred at room temperature for one hour, poured into water and extracted with ethyl ether, and the organic phase is separated out after settling has taken place, dried over magnesium sulphate and evaporated. The residue obtained is purified by chromatography on a column of silica eluted with a mixture of ethyl acetate and hexane (1/4 by volume). After evaporation of the solvents, 18.1 g (79%) of α-ethynyl-(5,6,7,8-tetrahydro-5,5,8,8-tetramethyl-2-naphthalene)methanol are collected, with a melting point of 56–7° C.

(c) Methyl 2-hydroxy-4-[3-hydroxy-3-(5,6,7,8-tetrahydro-5,5,8,8-tetramethyl-2-naphthyl)-1-propynyl]benzoate In a similar manner to Example 1(d), by reaction of 10.3 g (42.5 mmol) of α-ethynyl-(5,6,7,8-tetrahydro-5,5,8,8-tetramethyl-2-naphthalene)methanol with 11.8 g (42.5 mmol) of methyl 2-hydroxy-4-iodobenzoate, 13.6 g (82%) of the expected methyl ester are obtained, with a melting point of 92–3° C.

(d) Methyl 2-hydroxy-4-[3-(5,6,7,8-tetrahydro-5,5,8,8-tetramethyl-2-naphthyl)-1-propynyl]benzoate In a similar manner to Example 5(e), starting with 1 g (2.6 mmol) of the above methyl ester, 210 mg (22%) of methyl 2-hydroxy-4-[3-(5,6,7,8-tetrahydro-5,5,8,8-tetramethyl-2-naphthyl)-1-propynyl]benzoate are obtained, with a melting point of 75–7° C.

EXAMPLE 7

2-Hydroxy-4-[3-(5,6,7,8-tetrahydro-5,5,8,8-tetramethyl-2-naphthyl)-1-propynyl]benzoic acid (a) 2-Hydroxy-4-[3-hydroxy-3-(5,6,7,8-tetrahydro-5,5,8,8-tetramethyl-2-naphthyl)-1-propynyl]benzoic acid In a similar manner to Example 1(e), starting with 8.5 g (21.6 mmol) of methyl 2-hydroxy-4-[3-hydroxy-3-(5,6,7,8-tetrahydro-5,5,8,8-tetramethyl-2-naphthyl)-1-propynyl]benzoate, 7.8 g (95%) of the expected acid are obtained, with a melting point of 203° with decomposition.

(b) 2-Hydroxy-4-[3-(5,6,7,8-tetrahydro-5,5,8,8-tetramethyl-2-naphthyl)-1-propynyl]benzoic acid In a similar manner to Example 5(e) starting with 1 g (2.6 mmol) of 2-hydroxy-4-[3-hydroxy-3-(5,6,7,8-tetrahydro-5,5,8,8-tetramethyl-2-naphthyl)-1-propynyl]benzoic acid, 820 mg (86%) of 2-hydroxy-4-[3-(5,6,7,8-tetrahydro-5,5,8,8-tetramethyl-2-naphthyl)-1-propynyl]benzoic acid are obtained, with a melting point of 178–80° C.

EXAMPLE 8

2-Hydroxy-4-[3-(3-hydroxy-5,6,7,8-tetrahydro-5,5,8,8-tetramethyl-2-naphthyl)-1-propynyl]benzoic acid (a) 3-Methoxyethoxymethoxy-5,6,7,8-tetrahydro-5,5,8,8-tetramethyl-2-bromonaphthalene 720 mg (24 mmol) of sodium hydride (80% in oil) and 50 ml of DMF are introduced into a three-necked flask under a stream of nitrogen. A solution of 5.7 g (20 mmol) of 3-bromo-5,6,7,8-tetrahydro-5,5,8,8-tetramethyl-2-naphthol dissolved in 75 ml of DMF are added dropwise and the mixture is stirred until the evolution of gas has ceased. 6.8 ml (59.3 mmol) of methoxyethoxymethyl chloride are then added at 0° C. and the mixture is stirred for four hours. The reaction medium is poured into water and extracted with ethyl ether, and the organic phase is separated out after settling has taken place, dried over magnesium sulphate and evaporated. 16.6 g (91%) of the expected product are collected in the form of an oil.

(b) 3-Methoxyethoxymethoxy-5,6,7,8-tetrahydro-5,5,8,8-tetramethyl-2-naphthylcarboxaldehyde 16.3 g (44 mmol) of 3-methoxyethoxymethoxy-5,6,7,8-tetrahydro-5,5,8,8-tetramethyl-2-bromonaphthalene and 50 ml of THF are introduced into a three-necked flask under a stream of nitrogen. 19.3 ml of n-butyllithium (2.5 M in hexane) are added dropwise at −78° C. and the mixture is stirred for 30 minutes, followed by addition of 3.7 ml (48.4 mmol) of DMF, and the mixture is allowed to return to room temperature. The reaction medium is poured into aqueous ammonium chloride solution and extracted with ethyl ether, and the organic phase is separated out after settling has taken place, dried over magnesium sulphate and evaporated. 13.9 g (100%) of the expected aldehyde are collected in the form of an oil.

c) α-Trimethylsilylethynyl-(3-methoxyethoxymethoxy-5,6,7,8-tetrahydro-5,5,8,8-tetramethyl-2-naphthalene)methanol In a similar manner to Example 1(b), by reaction of 13.5 g (42.1 mmol) of 3-methoxyethoxy-methoxy-5,6,7,8-tetrahydro-5,5,8,8-tetramethyl-2-naphthylcarboxaldehyde with 7.1 ml (50.6 mmol) of trimethylsilylacetylene, 17.5 g (100%) of the expected alcohol are obtained in the form of a yellow oil.

d) α-Ethynyl-(3-methoxyethoxymethoxy-5,6,7,8-tetrahydro-5,5,8,8-tetramethyl-2-naphthalene)methanol In a similar manner to Example 1(c), starting with 17 g (40.6 mmol) of α-trimethylsilylethynyl-(3-methoxyethoxymethoxy-5,6,7,8-tetrahydro-5,5,8,8-tetramethyl-2-naphthalene)methanol, 12.4 g (88%) of α-ethynyl-(3-methoxyethoxymethoxy-5,6,7,8-tetrahydro-5,5,8,8-tetramethyl-2-naphthalene)methanol are obtained in the form of an oil.

(e) Methyl 2-hydroxy-4-[3-hydroxy-3-(3-methoxyethoxymethoxy-5,6,7,8-tetrahydro-5,5,8,8-tetramethyl-2-naphthyl)-1-propynyl]benzoate In a similar manner to Example 1(d), by reaction of 7.1 g (20.5 mmol) of α-ethynyl-(3-methoxyethoxymethoxy-5,6,7,8-tetrahydro-5,5,8,8-tetramethyl-2-naphthalene)methanol with 5.7 g (20.5 mmol) of methyl 2-hydroxy-4-iodobenzoate, 9.6 g (94%) of the methyl ester are obtained in the form of an oil.

(f) 2-Hydroxy-4-[3-hydroxy-3-(3-methoxyethoxymethoxy-5,6,7,8-tetrahydro-5,5,8,8-tetramethyl-2-naphthyl)-1-propynyl]benzoic acid In a similar manner to Example 1(e), starting with 9 g (21.6 mmol) of the above methyl ester, 7.8 g (89%) of the expected acid are obtained, with a melting point of 106–8° C.

(g) 2-Hydroxy-4-[3-(3-hydroxy-5,6,7,8-tetrahydro-5,5,8,8-tetramethyl-2-naphthyl)-1-propynyl]benzoic acid In a similar manner to Example 5(e), starting with 1.7 g (3.5 mmol) of 2-hydroxy-4-[3-hydroxy-3-(3-methoxyethoxymethoxy-5,6,7,8-tetrahydro-5,5,8,8-tetramethyl-2-naphthyl)-1-propynyl]benzoic acid, 670 mg (50%) of the expected acid are obtained, with a melting point of 216–7° C.

EXAMPLE 9

2-Hydroxy-4-[3-(5,6,7,8-tetrahydro-5,5,8,8-tetramethyl-2-naphthyl)-1-propynyl]benzenemethanol 760 mg (2.2 mmol) of methyl 2-hydroxy-4-[3-(5,6,7,8-tetrahydro-5,5,8,8-tetramethyl-2-naphthyl)-1-propynyl]benzoate and 20 ml of toluene are introduced into a three-necked flask under a stream of nitrogen. 4.4 ml of diisobutylaluminium hydride (1 M in toluene) are added at −78° C. and the mixture is allowed to return to room temperature. 9 ml of methanol and then 9 ml of hydrochloric acid (1 N) are successively introduced. The reaction medium is poured into an ethyl acetate/water mixture and the organic phase is separated out after settling has taken place, dried over magnesium sulphate and then evaporated. The residue is purified by chromatography on a column of silica eluted with a mixture of ethyl acetate and heptane (50/50% by volume). After evaporation of the solvents, 200 mg (30%) of the expected alcohol are collected, with a melting point of 94–5° C.

EXAMPLE 10

Diethanolamine 2-hydroxy-4-[3-(5,6,7,8-tetrahydro-5,5,8,8-tetramethyl-2-naphthyl)-1-propynyl]benzoate 100 mg (2.76 mmol) of 2-hydroxy-4-[3-(5,6,7,8-tetrahydro-5,5,8,8-tetramethyl-2-naphthyl)-1-propynyl]benzoic acid and 5 ml of methanol are introduced into a round-bottomed flask and 29 mg (2.76 mmol) of diethanolamine are added. The reaction medium is stirred for one hour and evaporated to dryness, and the residue obtained is triturated from a mixture of heptane and ethyl ether (50/50). The solid is filtered off and dried. 100 mg (78%) of diethanolamine salt are collected, with a melting point of 100–5° C.

EXAMPLE 11

Lithium 2-hydroxy-4-[3-(5,6,7,8-tetrahydro-5,5,8,8-tetramethyl-2-naphthyl)-1-propynyl]benzoate In a similar manner to Example 10, by reaction of 200 mg (5.5 mmol) of 2-hydroxy-4-[3-(5,6,7,8-tetrahydro-5,5,8,8-tetramethyl-2-naphthyl)-1-propynyl]benzoic acid with 23 mg (5.5 mmol) of lithium hydroxide hydrate, 150 mg (74%) of the expected lithium salt are obtained, with a melting point of 225–9° C.

EXAMPLE 12

4-[3-(5,6,7,8-Tetrahydro-5,5,8,8-tetramethyl-2-naphthyl)-2-propynyl]benzoic acid In a similar manner to Example 5(e), starting with 1.66 g (4.6 mmol) of 4-[1-hydroxy-3-(5,6,7,8-tetrahydro-5,5,8,8-tetramethyl-2-naphthyl)-2-propynyl]benzoic acid (prepared in Example 10(b) of patent EP 0,661,258), 310 mg (19.5%) of 4-[3-(5,6,7,8-tetrahydro-5,5,8,8-tetramethyl-2-naphthyl)-2-propynyl]benzoic acid are obtained, with a melting point of 159–60° C.

EXAMPLE 13

2-Hydroxy-4-[3-(4,4-dimethylthiochroman-6-yl)-1-propynyl]benzoic acid

In a similar manner to Example 5(e), starting with 750 mg (2 mmol) of 2-hydroxy-4-[3-hydroxy-3-(4,4-dimethylthiochroman-6-yl)-1-propynyl]benzoic acid (prepared in Example 19 of patent EP 0,661,258), and after chromatography on a column of silica eluted with a mixture of dichloromethane and methanol (80/20), 340 mg (28%) of 2-hydroxy-4-[3-(4,4-dimethylthiochroman-6-yl)-1-propynyl]benzoic acid are obtained, with a melting point of 195–6° C.

EXAMPLE 14

2-Hydroxy-4-[3-(8,8-dimethyl-5,6,7,8-tetrahydro-2-naphthyl)-1-propynyl]benzoic acid (a) Methyl 2-hydroxy-4-[3-oxo-3-(8,8-dimethyl-5,6,7,8-tetrahydro-2-naphthyl)-1-propynyl]benzoate 12 g (54 mmol) of 8,8-dimethyl-5,6,7,8-tetrahydro-2-naphthoyl chloride, 14.7 g (59 mmol) of methyl 2-hydroxy-4-trimethylsilylethynylbenzoate (prepared in Example 5(a) of patent EP 0,661,258) and 200 ml of dichloromethane are introduced into a round-bottomed flask. 21.6 g (162 mmol) of $AlCl_3$ are added portionwise at 0° C. and the mixture is stirred at room temperature for 8 hours. The reaction medium is poured into ice and extracted with dichloromethane, and the organic phase is separated out after settling has taken place, dried over magnesium sulphate and evaporated. The residue obtained is purified by chromatography on a column of silica eluted with a mixture of dichloromethane and hexane (50/50). 12.5 g (64%) of the expected product are collected, with a melting point of 114–6° C.

(b) Methyl 2-hydroxy-4-[3-hydroxy-3-(8,8-dimethyl-5,6,7,8-tetrahydro-2-naphthyl)-1-propynyl]benzoate 7.95 g (22 mol) of methyl 2-hydroxy-4-[3-oxo-3-(8,8-dimethyl-5,6,7,8-tetrahydro-2-naphthyl)-1-propynyl]benzoate, 150 ml of THF and 20 ml of methanol are introduced into a round-bottomed flask. 660 mg (17.4 mmol) of sodium borohydride are added portionwise and the mixture is stirred at room temperature for two hours. The reaction medium is poured into ice-water, neutralized with hydrochloric acid and extracted with ethyl acetate, and the organic phase is separated out after settling has taken place, washed with water, dried over magnesium sulphate and evaporated. The residue obtained is purified by chromatography on a column of silica eluted with a mixture of heptane and ethyl acetate (80/20). After evaporation of the solvents, 3.8 g (47.5%) of the expected product are collected in the form of an oil.

(c) Methyl 2-hydroxy-4-[3-(8,8-dimethyl-5,6,7,8-tetrahydro-2-naphthyl)-1-propynyl]benzoate In a similar manner to Example 5(e), starting with 4 g (11 m mol) of the above methyl ester, 1.13 g (29.5%) of methyl 2-hydroxy-4-[3-(8,8-dimethyl-5,6,7,8-tetrahydro-2-naphthyl)-1-propynyl]benzoate are obtained in the form of an orange-coloured oil.

(d) 2-Hydroxy-4-[3-(8,8-dimethyl-5,6,7,8-tetrahydro-2-naphthyl)-1-propynyl]benzoic acid In a similar manner to Example 1(e), starting with 1 g (2.9 mmol) of the above methyl ester, 370 mg (39%) of 2-hydroxy-4-[3-(8,8-dimethyl-5,6,7,8-tetrahydro-2-naphthyl)-1-propynyl]benzoic acid are obtained, with a melting point of 185–7° C.

EXAMPLE 15

2-Hydroxy-4-[3-(5,5-dimethyl-5,6,7,8-tetrahydro-2-naphthyl)-1-propynyl]benzoic acid (a) Methyl 2-hydroxy-4-[3-oxo-3-(5,5-dimethyl-5,6,7,8-tetrahydro-2-naphthyl)-1-propynyl]benzoate In a similar manner to Example 14(a), by reaction of 4.7 g (21 mmol) of 5,5-dimethyl-5,6,7,8-tetrahydro-2-naphthoyl chloride with 5.7 g (22.8 mmol) of methyl 2-hydroxy-4-trimethylsilylethynylbenzoate (prepared in Example 5(a) of patent EP 0,661,258), 5.14 g (68.5%) of the expected methyl ester are obtained, with a melting point of 89–90° C.

(b) Methyl 2-hydroxy-4-[3-hydroxy-3-(5,5-dimethyl-5,6,7,8-tetrahydro-2-naphthyl)-1-propynyl]benzoate In a similar manner to Example 14(b), starting with 2.4 g (6.6 mmol) of methyl 2-hydroxy-4-[3-oxo-3-(5,5-dimethyl-5,6,7,8-tetrahydro-2-naphthyl)-1-propynyl]benzoate, 1.6 g (67%) of methyl 2-hydroxy-4-[3-hydroxy-3-(5,5-dimethyl-5,6,7,8-tetrahydro-2-naphthyl)-1-propynyl]benzoate are obtained in the form of an orange-coloured oil.

(c) 2-Hydroxy-4-[3-hydroxy-3-(5,5-dimethyl-5,6,7,8-tetrahydro-2-naphthyl)-1-propynyl]benzoic acid In a similar manner to Example 1(e), starting with 1.61 g (4.4 mmol) of the above methyl ester, 1.2 g (77.4%) of the expected acid are obtained, with a melting point of 141–2° C.

(d) 2-Hydroxy-4-[3-(5,5-dimethyl-5,6,7,8-tetrahydro-2-naphthyl)-1-propynyl]benzoic acid In a similar manner to Example 5(e), starting with 580 mg (1.65 mmol) of 2-hydroxy-4-[3-hydroxy-3-(5,5-dimethyl-5,6,7,8-tetrahydro-2-naphthyl)-1-propynyl]benzoic acid, 470 mg (85%) of 2-hydroxy-4-[3-(5,5-dimethyl-5,6,7,8-tetrahydro-2-naphthyl)-1-propynyl]benzoic acid are obtained, with a melting point of 152–3° C.

EXAMPLE 16

Ethyl 4-[3-(5,6,7,8-tetrahydro-5,5,8,8-tetramethyl-2-naphthyl)-1-propynyl]benzoate (a) Methoxyallene 210 ml (2.5 mol) of propargyl methyl ether and 12 g (0.11 mol) of potassium tert-butoxide are introduced into a three-necked flask under argon. The reaction medium is refluxed for three hours and distilled at atmospheric pressure, and the fraction passing at 51° C. is collected. 153.5 g (88%) of the expected product are obtained in the form of a colourless oil.

(b) 3-(5,6,7,8-Tetrahydro-5,5,8,8-tetramethyl-2-naphthyl)-1-propyne 20 g (0.82 mol) of magnesium activated with 0.1 ml of dibromoethane are introduced into a four litre reactor under a stream of nitrogen. A solution of 200 g (0.75 mol) of 2-bromo-5,6,7,8-tetrahydro-5,5,8,8-tetramethylnaphthalene is added dropwise so as to maintain the reflux of the THF and the mixture is stirred at 50° C. for two hours. The reaction medium is then cooled to –5° C. and 1.2 g (8.2 mmol) of CuBr are added and a solution of 58 g (0.82 mol) of methoxyallene in 100 ml of THF is introduced dropwise. The mixture is stirred for one hour at –5° C. and is then allowed to return to room temperature and is stirred for two hours. The reaction medium is poured into saturated ammonium chloride solution and extracted with ethyl acetate, and the organic phase is separated out after settling has taken place, dried over magnesium sulphate and evaporated. The oil obtained is distilled at 0.02 mm Hg and the fraction passing at 95–100° C. is collected. 79 g (47%) of the expected product are obtained in the form of a colourless oil.

(c) Ethyl 4-[3-(5,6,7,8-tetrahydro-5,5,8,8-tetramethyl-2-naphthyl)-1-propynyl]benzoate 7.4 g (32.7 mmol) of 3-(5,6,7,8-tetrahydro-5,5,8,8-tetramethyl-2-naphthyl)-1-propyne, 8.2 g (29.7 mmol) of ethyl 4-iodobenzoate and 50 ml of triethylamine are introduced into a three-necked flask under a stream of nitrogen. The reaction medium is degassed by bubbling nitrogen through, 360 mg (0.5 mmol) of bis(triphenylphosphine)palladium(II) chloride and 130 mg of copper iodide are introduced and the mixture is stirred at room temperature for eight hours. The reaction medium is evaporated to dryness, the residue is taken up in ethyl acetate and hydrochloric acid (1 N) and the organic phase is separated out after settling has taken place, dried over magnesium sulphate and evaporated. The residue is purified by chromatography on a column of silica eluted with a mixture of heptane and ethyl acetate (70/30). After evaporation of the solvents, a solid is collected which is triturated from heptane, filtered and dried.

9.3 g (84%) of the expected ethyl ester are collected, with a melting point of 59–60° C.

EXAMPLE 17

4-[3-(5,6,7,8-Tetrahydro-5,5,8,8-tetramethyl-2-naphthyl)-1-propynyl]benzamide (a) 4-[3-(5,6,7,8-Tetrahydro-5,5,8,8-tetramethyl-2-naphthyl)-1-propynyl]benzoic acid In a similar manner to Example 16(c), by reaction of 8 g (35.3 mmol) of 3-(5,6,7,8-tetrahydro-5,5,8,8-tetramethyl-2-naphthyl)-1-propyne with 8 g (32.1 mmol) of 4-iodobenzoic acid, 10.4 g (94%) of the expected acid are obtained, with a melting point of 167–8° C.

(b) 4-[3-(5,6,7,8-Tetrahydro-5,5,8,8-tetramethyl-2-naphthyl)-1-propynyl]benzoyl chloride 2.9 g (8.3 mmol) of 4-[3-(5,6,7,8-tetrahydro-5,5,8,8-tetramethyl-2-naphthyl)-1-propynyl]benzoic acid and 100 ml of dichloromethane are introduced into a round-bottomed flask under a stream of nitrogen and 2.4 ml (12.1 mmol) of dicyclohexylamine are added dropwise. The mixture is stirred at room temperature for one hour, 1.2 ml (11.7 mmol) of thionyl chloride are added dropwise and the mixture is stirred for one hour. The reaction medium is evaporated to dryness, the residue is taken up in ethyl ether, the dicyclohexylamine salt is filtered off and the filtrate is evaporated. 3 g (100%) of the crude acid chloride are collected, which product will be used in its current state for the rest of the synthesis.

(c) 4-[3-(5,6,7,8-Tetrahydro-5,5,8,8-tetramethyl-2-naphthyl)-1-propynyl]benzamide 3 g (8.3 mmol) of the above acid chloride dissolved in 100 ml of THF are introduced into a round-bottomed flask, 1 ml (9.1 mmol) of aqueous ammonia (32%) is added and the mixture is stirred at room temperature for one hour. The reaction medium is poured into water and extracted with dichloromethane, and the organic phase is separated out after settling has taken place, washed with water, dried over magnesium sulphate and evaporated. The solid obtained is triturated from heptane, filtered and dried. 2.5 g (87%) of 4-[3-(5,6,7,8-tetrahydro-5,5,8,8-tetramethyl-2-naphthyl)-1-propynyl]benzamide are collected, with a melting point of 207–8° C.

EXAMPLE 18

N-Ethyl-4-[3-(5,6,7,8-tetrahydro-5,5,8,8-tetramethyl-2-naphthyl)-1-propynyl]benzamide In a similar manner to Example 17(b), by reaction of 3 g (8.3 mmol) of 4-[3-(5,6,7,8-tetrahydro-5,5,8,8-tetramethyl-2-naphthyl)-1-propynyl]benzoyl chloride with 650 μl (10 mmol) of ethylamine (70%), 1.84 g (59.4%) of the expected ethyl amide are obtained, with a melting point of 128–9° C.

EXAMPLE 19

4-[3-(5,6,7,8-Tetrahydro-5,5,8,8-tetramethyl-2-naphthyl)-1-propynyl]benzoic acid morpholide In a similar manner to Example 17(b), by reaction of 1.25 g (3.4 mmol) of 4-[3-(5,6,7,8-tetrahydro- 5,5,8,8-tetramethyl-2-naphthyl)-1-propynyl]benzoyl chloride with 320 μl (3.8 mmol) of morpholine, 430 mg (31%) of 4-[3-(5,6,7,8-tetrahydro-5,5,8,8-tetramethyl-2-naphthyl)-1-propynyl]benzoic acid morpholide are obtained, with a melting point of 98–9° C.

EXAMPLE 20

N-(4-Hydroxyphenyl)-4-[3-(5,6,7,8-tetrahydro-5,5,8, 8-tetramethyl-2-naphthyl)-1-propynyl]benzamide In a similar manner to Example 17(b), by reaction of 3 g (8.3 mmol) of 4-[3-(5,6,7,8-tetrahydro-5,5,8,8-tetramethyl-2-naphthyl)-1-propynyl]benzoyl chloride with 1 g (9.2 mmol) of 4-aminophenol, 1.94 g (54%) of N-(4-hydroxyphenyl)-4-[3-(5,6,7,8-tetrahydro-5,5,8,8-tetramethyl-2-naphthyl)-1-propynyl]benzamide are obtained, with a melting point of 159–60° C.

EXAMPLE 21

4-[3-(5,6,7,8-Tetrahydro-5,5,8,8-tetramethyl-2-naphthyl)-1-propynyl]benzenemethanol In a similar manner to Example 16(c), by reaction of 3.67 g (16.2 mmol) of 3-(5,6,7,8-tetrahydro-5,5,8,8-tetramethyl-2-naphthyl)-1-propyne with 3.45 g (14.8 mmol) of 4-iodobenzenemethanol, 4.9 g (100%) of 4-[3-(5,6,7,8-tetrahydro-5,5,8,8-tetramethyl-2-naphthyl)-1-propynyl]benzenemethanol are obtained in the form of a viscous orange oil.

$^1$H NMR (CDCl$^3$, 250 MHz) 1.27 (6H, s), 1.29 (6H, s), 1.68 (4H, s), 3.77 (2H, s), 4.67 (2H, d), 7.17 (1H Ar, dd), 7.27 (2H Ar, d), 7.30 (2H Ar, d), 7.42 (2H Ar, c).

EXAMPLE 22

4-[3-(5,6,7,8-Tetrahydro-5,5,8,8-tetramethyl-2-naphthyl)-1-propynyl]benzaldehyde 1.3 g (4 mmol) of 4-[3-(5,6,7,8-tetrahydro-5,5,8,8-tetramethyl-2-naphthyl)-1-propynyl]benzenemethanol and 20 ml of dichloromethane are introduced into a round-bottomed flask and 3.4 g (39.2 mmol) of manganese oxide are added. The mixture is stirred at room temperature for eight hours. Magnesium sulphate is added to the reaction medium, the mixture is filtered and the filtrate is evaporated. The residue obtained is purified by chromatography on a column of silica eluted with a mixture of ethyl acetate and heptane (10/90). After evaporation of the solvents, 930 mg (29.5%) of 4-[3-(5,6,7,8-tetrahydro-5,5,8,8-tetramethyl-2-naphthyl)-1-propynyl]benzaldehyde are collected in the form of a yellow oil.

$^1$H NMR (CDCl$_3$, 250 MHz) 1.28 (6H, s), 1.30 (6H, s), 1.69 (4H, s), 3.81 (2H, s), 7.20 (1H Ar, dd), 7.31 (2H Ar, c), 7.59 (2H Ar, d), 7.80 (2H Ar, d), 9.99 (1H, s).

EXAMPLE 23

4-[3-(5,6,7,8-Tetrahydro-5,5,8,8-tetramethyl-2-naphthyl)-1-propynyl]phenol

In a similar manner to Example 16(c), by reaction of 1.13 g (5 mmol) of 3-(5,6,7,8-tetrahydro- 5,5,8,8-tetramethyl-2-naphthyl)-1-propyne with 1 g (4.5 mmol) of 4-iodophenol, 1.28 g (88%) of 4-[3-(5,6,7,8-tetrahydro-5,5,8,8-tetramethyl-2-naphthyl)-1-propynyl]phenol are obtained in the form of a viscous orange-red oil.

$^1$H NMR (CDCl$_3$, 250 MHz) 1.27 (6H, s), 1.29 (6H, s), 1.68 (4H, s), 3.75 (2H, s), 5.05 (1H, s), 6.76 (2H, d), 7.20 (1H Ar, dd), 7.25 (1H, d), 7.31 (3H Ar, c).

EXAMPLE 24

4-[3-(5,6,7,8-Tetrahydro-5,5,8,8-tetramethyl-2-naphthyl)-1-propynyl]toluene

In a similar manner to Example 16(c), by reaction of 1.62 g (7.15 mmol) of 3-(5,6,7,8-tetrahydro-5,5,8,8-tetramethyl-2-naphthyl)-1-propyne with 1.42 g (6.5 mmol) of 4-iodotoluene, 1.29 g (63%) of 4-[3-(5,6,7,8-tetrahydro-5,5,8,8-tetramethyl-2-naphthyl)-1-propynyl]toluene are obtained in the form of a yellowish oil.

$^1$H NMR (CDCl$_3$, 250 MHz) 1.27 (6H, s), 1.29 (6H, s), 1.69 (4H, s), 2.33 (3H, s), 3.81 (2H, s), 7.20 (1H Ar, dd), 7.31 (2H Ar, c), 7.59 (2H Ar, d), 7.80 (2H Ar, d).

EXAMPLE 25

Hexyl 4-[3-(5,6,7,8-tetrahydro-5,5,8,8-tetramethyl-2-naphthyl)-1-propynyl]benzoate 2 g (5.8 mmol) of 4-[3-(5,6,7,8-tetrahydro-5,5,8,8-tetramethyl-2-naphthyl)-1-propynyl]benzoic acid, 30 ml of DMF, 2 drops of 15-crown-5 and 2 g (23.8 mmol) of sodium bicarbonate are introduced into a round-bottomed flask. 3.1 ml (20.8 mmol) of 1-iodohexane are added and the mixture is stirred at room temperature for 24 hours. The reaction medium is poured into water and extracted with ethyl acetate and the organic phase is separated out after settling has taken place, washed with water, dried over magnesium sulphate and evaporated. 2 g (80%) of the expected hexyl ester are collected in the form of a pale red oil.

$^1$H NMR (CDCl$_3$, 250 MHz) 0.9 (3H, t), 1.27 (6H, s), 1.29 (6H, s), 1.34 (6H, c), 1.66 (4H, s), 1.72 (2H, m), 3.81 (2H, s), 4.30 (2H, t), 7.20 (1H Ar, dd), 7.31 (2H Ar, c), 7.50 (2H Ar, d), 7.95 (2H Ar, d).

EXAMPLE 26

N-Hydroxy-2-hydroxy-4-[3-(5,6,7,8-tetrahydro-5,5,8,8-tetramethyl-2-naphthyl)-1-propynyl]benzamide (a) N-Hydroxy-2-hydroxy-4-iodobenzamide 23.3 g (84 mmol) of methyl 2-hydroxy-4-iodobenzoate and 360 ml of sodium hydroxide solution (1 N) are introduced into a three-necked flask under a stream of nitrogen. 8 g (113 mmol) of hydroxylamine hydrochloride are added and the mixture is stirred at room temperature for two hours. The reaction medium is adjusted to pH 7–8 with concentrated hydrochloric acid and the solid is filtered off. The solid is dissolved in ethyl acetate and washed with water, and the organic phase is separated out after settling has taken place, dried over magnesium sulphate and evaporated. The residue is triturated from heptane, filtered and dried. 17.6 g (71.5%) of the expected product are collected, with a melting point of 195–6° C.

(b) N-Hydroxy-2-hydroxy-4-[3-(5,6,7,8-tetrahydro-5,5,8,8-tetramethyl-2-naphthyl)-1-propynyl]benzamide In a similar manner to Example 16(c), by reaction of 4 g (17.7 mmol) of 3-(5,6,7,8-tetrahydro-5,5,8,8-tetramethyl-2-naphthyl)-1-propyne with 4.1 g (14.7 mmol) of N-hydroxy-2-hydroxy-4-iodobenzamide, 550 mg (10%) of N-hydroxy-2-hydroxy-4-[3-(5,6,7,8-tetrahydro-5,5,8,8-tetramethyl-2-naphthyl)-1-propynyl]benzamide are obtained, with a melting point of 119–20° C.

EXAMPLE 27

2-Methyl-4-[3-(5,6,7,8-tetrahydro-5,5,8,8-tetramethyl-2-naphthyl)-1-propynyl]benzoic acid In a similar manner to Example 16(c), by reaction of 10 g (44.2 mmol) of 3-(5,6,7,8-tetrahydro-5,5,8,8-tetramethyl-2-naphthyl)-1-propyne with 6.5 g (29.5 mmol) of 4-bromo-2-methylbenzoic acid, 1.18 g (11%) of 2-methyl-4-[3-(5,6,7,8-tetrahydro-5,5,8,8-tetramethyl-2-naphthyl)-1-propynyl]benzoic acid are obtained, with a melting point of 149–50° C.

EXAMPLE 28

3-Methyl-4-[3-(5,6,7,8-tetrahydro-5,5,8,8-tetramethyl-2-naphthyl)-1-propynyl]benzoic acid In a similar manner to Example 16(c), by reaction of 10 g (44.2 mmol) of 3-(5,6,7,8-tetrahydro-5,5,8,8-tetramethyl-2-naphthyl)-1-propyne with 6.5 g (29.5 mmol) of 4-bromo-3-methylbenzoic acid, 1.1 g (11%) of 3-methyl-4-[3-(5,6,7,8-tetrahydro-5,5,8,8-tetramethyl-2-naphthyl)-1-propynyl]benzoic acid are obtained, with a melting point of 196–7° C.

EXAMPLE 29

6-[3-(5,5,8,8-Tetramethyl-5,6,7,8-tetrahydro-2-naphthyl)propa-1,2-dienyl]nicotinic acid (a) Methyl 6-[3-(5,5,8,8-tetramethyl-5,6,7,8-tetrahydro-2-naphthyl)propa-1,2-dienyl]nicotinate In a similar manner to Example 16(c), by reaction of 920 mg (4.1 mmol) of 3-(5,6,7,8-tetrahydro-5,5,8,8-tetramethyl-2-naphthyl)-1-propyne with 1.1 g (4.2 mmol) of methyl 4-iodonicotinate, 260 mg (18%) of methyl 6-[3-(5,5,8,8-tetramethyl-5,6,7,8-tetrahydro-2-naphthyl)propa-1,2-dienyl]nicotinate are obtained in the form of an orange-coloured oil.

$^1$H NMR (CDCl$_3$, 250 MHz) 1.34 (12H, s), 1.75 (4H, s), 3.87 (3H, s), 6.56 (1H, d), 6.92 (1H, d), 7.19 (1H, d), 7.29 (1H, dd), 7.42 (2H, t), 7.50 (1H, d), 9.10 (1H, s).

(b) 6-[3-(5,5,8,8-Tetramethyl-5,6,7,8-tetrahydro-2-naphthyl)propa-1,2-dienyl]-3-nicotinic acid 370 mg (1 mmol) of the above methyl ester, 10 ml of THF and 5 ml of methanolic sodium hydroxide solution (2 N) are introduced into a round-bottomed flask. The mixture is heated at 40° C. for one hour and evaporated to dryness, the residue is taken up in water, the pH is adjusted to 5 with hydrochloric acid, the mixture is extracted with ethyl acetate and the organic phase is separated out after settling has taken place, dried over magnesium sulphate and evaporated. The residue is triturated from heptane, filtered and dried. 240 mg (66%) of the expected acid are collected, with a melting point of 224–5° C.

EXAMPLE 30

4-[3-(5,5,8,8-Tetramethyl-5,6,7,8-tetrahydro-2-nahthyl)propa-1,2-dienyl]benzoic acid 6.02 g (16 mmol) of ethyl 4-[3-(5,6,7,8-tetrahydro-5,5,8,8-tetramethyl-2-naphthyl)-1-propynyl]benzoate, 5 ml of methanol, 5 ml of THF and 50 ml of heptane are introduced into a round-bottomed flask. 850 mg of sodium hydroxide are added and the mixture is refluxed for one hour. The reaction medium is poured into water, adjusted to pH 1 with hydrochloric acid and extracted with ethyl acetate, and the organic phase is separated out after settling has taken place, dried over magnesium sulphate and evaporated. The residue obtained is triturated from ethyl alcohol, filtered and dried. 1.37 g (24.5%) of 4-[3-(5,5,8,8-tetramethyl-5,6,7,8-tetrahydro-2-naphthyl)propa-1,2-dienyl]benzoic acid are collected, with a melting point of 227–8° C.

EXAMPLE 31

2-Hydroxy-4-[3-(5,6,7,8-tetrahydro-5,5,8,8-tetramethyl-2-naphthyl)-1-butynyl]benzoic acid In a similar manner to Example 5(e), starting with 1 g (2.55 mmol) of 2-hydroxy-4-[3-hydroxy-3-(5,6,7,8-tetrahydro-5,5,8,8-tetramethyl-2-naphthyl)-1-butynyl] benzoic acid (prepared in Example 30 of patent EP 0,661, 258), 450 mg (47%) of 2-hydroxy-4-[3-(5,6,7,8-tetrahydro-5,5,8,8-tetramethyl-2-naphthyl)-1-butynyl]benzoic acid are obtained, with a melting point of 191–2° C.

EXAMPLE 32

Various specific formulations based on compounds according to the invention are illustrated in this example.

A - ORAL ROUTE (a) 0.2 g tablet

| | |
|---|---|
| Compound of Example 2 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable suspension in 5 ml ampules

| | |
|---|---|
| Compound of Example 6 | 0.001 g |
| Glycerol | 0.500 g |
| 70% Sorbitol | 0.500 g |
| Sodium saccharinate | 0.010 g |
| Methyl para-hydroxybenzoate | 0.040 g |
| Flavouring qs | |
| Purified water qs | 5 ml |

(c) 0.8 g tablet

| | |
|---|---|
| Compound of Example 5 | 0.500 g |
| Pregelatinized starch | 0.100 g |
| Microcrystalline cellulose | 0.115 g |
| Lactose | 0.075 g |
| Magnesium stearate | 0.010 g |

(d) Drinkable suspension in 10 ml ampules

| | |
|---|---|
| Compound of Example 2 | 0.05 g |
| Glycerol | 1.000 g |
| 79% Sorbitol | 1.000 g |
| Sodium saccharinate | 0.010 g |
| Methyl para-hydroxybenzoate | 0.080 g |
| Flavouring qs | |
| Purified water qs | 10 ml |

B - TOPICAL ROUTE (a) Ointment

| | |
|---|---|
| Compound of Example 9 | 0.020 g |
| Isopropyl myristate | 81.700 g |
| Liquid petroleum jelly | 9.100 g |
| Silica ("Aerosil 200" sold by Degussa) | 9.180 g |

(b) Ointment

| | |
|---|---|
| Compound of Example 7 | 0.300 g |
| White petroleum jelly codex | 100 g |

(c) Nonionic water-in-oil cream

| | |
|---|---|
| Compound of Example 25 | 0.100 g |
| Mixture of emulsifying lanolin alcohols, waxes and oils ("anhydrous eucerin" sold by BDF) | 39.900 g |
| Methyl para-hydroxybenzoate | 0.075 g |
| Propyl para-hydroxybenzoate | 0.075 g |
| Sterile demineralized water qs | 100 g |

(d) Lotion

| | |
|---|---|
| Compound of Example 8 | 0.100 g |
| Polyethylene glycol (PEG 400) | 69.900 g |
| 95% Ethanol | 30.000 g |

(e) Hydrophobic ointment

| | |
|---|---|
| Coumpound of Example 20 | 0.300 g |
| Isopropyl myristate | 36.400 g |
| Silicone oil ("Rhodorsil 47 V 300" sold by Rhône-Poulenc) | 36.400 g |
| Beeswax | 13.600 g |
| Silicone oil ("Abil 300,000 cst" sold by Goldschmidt) | 100 g |

(f) Nonionic oil-in-water cream

| | |
|---|---|
| Compound of Example 30 | 0.500 g |
| Cetyl alcohol | 4.000 g |
| Glyceryl monostearate | 2.500 g |
| PEG-50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water | 100 g |

What is claimed is:

1. A propynyl biaromatic compound, having the general formula (I) below:

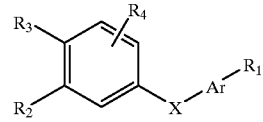

in which:

$R_1$ is
  (i) the —$CH_3$ radical
  (ii) the radical —$CH_2$—O—$R_6$
  (iii) the radical —O—$R_6$, or
  (iv) the radical —CO—$R_7$ $R_6$ and $R_7$ having the meanings given below, Ar is a radical selected from the group consisting of (a)–(e) below:

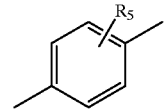

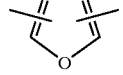

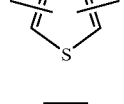

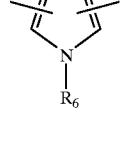

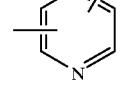

$R_5$ and $R_6$ have the meanings given below,
X is a radical of formula:

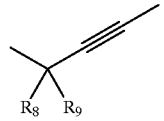 or 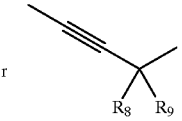 or 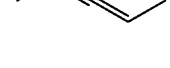

$R_8$ and $R_9$ have the meanings given below,
$R_2$ and $R_3$, which may be identical or different, are selected from the following:

(i) a hydrogen atom,
(ii) a linear or branched alkyl radical having from 1 to 20 carbon atoms,
(iii) a radical —OR$_6$,
(iv) a radical —SR$_6$, R$_6$ is defined below, wherein R$_2$ and R$_3$, taken together, may form, with the adjacent aromatic ring, a 5- or 6-membered ring optionally substituted with methyl groups and/or optionally interrupted by an oxygen or sulfur atom, wherein R$_2$ and R$_3$ cannot simultaneously have the meanings (i), (iii) and (iv) mentioned above, R$_4$ and R$_5$, which may be identical or different, are hydrogen atom, a halogen atom, a linear or a branched alkyl radical having from 1 to 20 carbon atoms or a radical —OR$_6$, wherein if R$_4$ is a hydroxyl radical, then R$_2$ and R$_3$ form, with the adjacent aromatic ring, a 5- or 6-membered ring which optionally is substituted with methyl groups and/or optionally interrupted by an oxygen or a sulfur atom, R$_6$ is a hydrogen atom, a lower alkyl radical or a radical —COR$_{10}$ R$_{10}$ is defined below, R$_7$ is selected from the following:
(a) a hydrogen atom
(b) a lower alkyl radical
(c) a radical of formula:

$$\diagdown N \diagup \begin{matrix} R'' \\ R' \end{matrix}$$

wherein R' and R" are defined below,
(d) a radical —OR$_{11}$,
(e) a radical —NHOR$_6$, R$_{11}$ is defined below, R$_8$ and R$_9$, if considered separately, are the same and are either a hydrogen atom or a radical —OR$_{10}$, or R$_8$ and R$_9$ are different, and one of them is a hydrogen atom and the other is a lower alkyl radical, or, R$_8$ and R$_9$ together form a ring —Y—(CH$_2$)$_n$—Y—, with Y representing an oxygen or a sulfur atom and with n equal to 2 or 3, R$_{10}$ is a lower alkyl radical, R$_{11}$ is a hydrogen atom, a linear or branched alkyl radical having from 1 to 20 carbon atoms, an alkenyl radical, a mono- or polyhydroxyalkyl radical, an optionally substituted aryl or aralkyl radical, a sugar residue or an amino acid or peptide residue, R' and R", which may be identical or different, are selected from a hydrogen atom, a lower alkyl radical, a mono- or polyhydroxyalkyl radical, an optionally substituted aryl radical or an amino acid or sugar residue, or alternatively, taken together, form a heterocycle, or a salt or optical or geometric isomer of said compound.

2. A compound having the general formula (II) below:

(II)

in which R$_1$ and Ar are defined according to claim 1 and wherein R'$_2$ and R'$_4$, which may be identical or different, are each a linear or branched alkyl radical having from 1 to 20 carbon atoms.

3. A compound according to claim 1, wherein said compound is selected from the group consisting of alkali metal, alkaline earth metal, zinc, and organic amine salts.

4. A compound according to claim 1, which is selected from the group consisting of:
4-[3-(3,5-di-tert-butyl-4-hydroxyphenyl)-1-propynyl]benzoic acid,
2-hydroxy-4-[3-(3,5-di-tert-butyl-4-hydroxyphenyl)-1-propynyl]benzoic acid,
4-[3-(5,6,7,8-tetrahydro-5,5,8,8-tetramethyl-2-naphthyl)-1-propynyl]benzoic acid,
methyl 2-hydroxy-4-[3-(5,6,7,8-tetrahydro-5,5,8,8-tetramethyl-2-naphthyl)-1-propynyl]benzoate,
2-hydroxy-4-[3-(5,6,7,8-tetrahydro-5,5,8,8-tetramethyl-2-naphthyl)-1-propynyl]benzoic acid,
2-hydroxy-4-[3-(3-hydroxy-5,6,7,8-tetrahydro-5,5,8,8-tetramethyl-2-naphthyl)-1-propynyl]benzoic acid,
2-hydroxy-4-[3-(5,6,7,8-tetrahydro-5,5,8,8-tetramethyl-2-naphthyl)-1-propynyl]benzenemethanol,
diethanolamine 2-hydroxy-4-[3-(5,6,7,8-tetrahydro-5,5,8,8-tetramethyl-2-naphthyl)-1-propynyl]benzoate,
lithium 2-hydroxy-4-[3-(5,6,7,8-tetrahydro-5,5,8,8-tetramethyl-2-naphthyl)-1-propynyl]benzoate,
4-[3-(5,6,7,8-tetrahydro-5,5,8,8-tetramethyl-2-naphthyl)-2-propynyl]benzoic acid,
2-hydroxy-4-[3-(4,4-dimethylthiochroman-6-yl)-1-propynyl]benzoic acid,
2-hydroxy-4-[3-(8,8-dimethyl-5,6,7,8-tetrahydro-2-naphthyl)-1-propynyl]benzoic acid,
2-hydroxy-4-[3-(5,5-dimethyl-5,6,7,8-tetrahydro-2-naphthyl)-1-propynyl]benzoic acid,
ethyl 4-[3-(5,6,7,8-tetrahydro-5,5,8,8-tetramethyl-2-naphthyl)-1-propynyl]benzoate,
4-[3-(5,6,7,8-tetrahydro-5,5,8,8-tetramethyl-2-naphthyl)-1-propynyl]benzamide,
N-ethyl-4-[3-(5,6,7,8-tetrahydro-5,5,8,8-tetramethyl-2-naphthyl)-1-propynyl]benzamide,
4-[3-(5,6,7,8-tetrahydro-5,5,8,8-tetramethyl-2-naphthyl)-1-propynyl]benzoic acid morpholide,
N-(4-hydroxyphenyl)-4-[3-(5,6,7,8-tetrahydro-5,5,8,8-tetramethyl-2-naphthyl)-1-propynyl]benzamide,
4-[3-(5,6,7,8-tetrahydro-5,5,8,8-tetramethyl-2-naphthyl)-1-propynyl]benzaldehyde,
4-[3-(5,6,7,8-tetrahydro-5,5,8,8-tetramethyl-2-naphthyl)-1-propynyl]phenol,
[3-(5,6,7,8-tetrahydro-5,5,8,8-tetramethyl-2-naphthyl)-1-propynyl]benzenemethanol,
4-[3-(5,6,7,8-tetrahydro-5,5,8,8-tetramethyl-2-naphthyl)-1-propynyl]toluene,
hexyl 4-[3-(5,6,7,8-tetrahydro-5,5,8,8-tetramethyl-2-naphthyl)-1-propynyl]benzoate,
N-hydroxy-4-[3-(5,6,7,8-tetrahydro-5,5,8,8-tetramethyl-2-naphthyl)-1-propynyl]benzamide, N-hydroxy-2-hydroxy-4-[3-(5,6,7,8-tetrahydro-5,5,8,8-tetramethyl-2-naphthyl)-1-propynyl]benzamide,
2-methyl-4-[3-(5,6,7,8-tetrahydro-5,5,8,8-tetramethyl-2-naphthyl)-1-propynyl]benzoic acid,
3-methyl-4-[3-(5,6,7,8-tetrahydro-5,5,8,8-tetramethyl-2-naphthyl)-1-propynyl]benzoic acid,
6-[3-(5,5,8,8-tetramethyl-5,6,7,8-tetrahydro-2-naphthyl)propa-1,2-dienyl]nicotinic acid,
4-[3-(5,5,8,8-tetra-methyl-5,6,7,8-tetrahydro-2-naphthyl)propa-1,2-dienyl]benzoic acid,
2-hydroxy-4-[3-(5,5,8,8-tetramethyl-5,6,7,8-tetrahydro-2-naphthyl)propa-1,2-dienyl]benzoic acid,
2-hydroxy-4-[3-(5,6,7,8-tetrahydro-5,5,8,8-tetramethyl-2-naphthyl)-1-butynyl]benzoic acid,
5-[3-(5,6,7,8-tetrahydro-5,5,8,8-tetramethyl-2-naphthyl)-1-propynyl]-2-pyridinecarboxylic acid,
4-[3-(3,5,5,8,8-pentamethyl-5,6,7,8-tetrahydro-2-naphthyl)-1-propynyl]benzoic acid,
2-[3-(5,6,7,8-tetrahydro-5,5,8,8-tetramethyl-2-naphthyl)-1-propynyl]-4-thiophenecarboxylic acid,
2-[3-(3,5,5,8,8-pentamethyl-5,6,7,8-tetrahydro-2-naphthyl)-1-propynyl]-4-thiophenecarboxylic acid,
2-hydroxy-4-[3-(3-tert-butyl-4-methoxyphenyl)-1-propynyl]benzoic acid,
2-hydroxy-4-[3-(3-tert-butyl-4-hydroxyphenyl)-1-propynyl]benzoic acid.

5. A compound according to claim 3, selected from the group consisting of:
4-[3-(3,5-di-tert-butyl-4-oxo-2,5-cyclohexadien-1-ylidene)-1-propynyl]benzoic acid, and
2-hydroxy-4-[3-(3,5-di-tert-butyl-4-oxo-2,5-cyclohexadien-1-ylidene)-1-propynyl]benzoic acid.

6. A compound according to claim 1, which has at least one of the following characteristics:
$R_1$ represents the radical —CO—$R_7$,
Ar represents the radicals of formula (a) or (e).

7. A compound according to one of claim 1, in which $R_8$ and $R_9$ are both hydrogen atoms or one of them represents a hydrogen atom and the other represents a lower alkyl radical.

8. A method of therapy comprising administration of a therapeutically effective amount of at least one compound of formula (I) or (II) according to claim 1.

9. A method for therapy which involves the administration of a therapeutically effective amount of a compound according to claim 1, wherein the condition treated is selected from the group consisting of dermatological conditions, inflammatory conditions, opthamological disorders, cancerous or precancerous conditions, alopecia, cardiovascular conditions, and insulin-dependent diabetes.

10. The method of claim 9, wherein said dermatological condition is selected from the group consisting of:
(i) conditions associated with keratinization, which optionally are associated with differentiation and/or proliferation;
(ii) keratinization disorders having an immunological and/or immunoallergic component;
(iii) dermal and epidermal proliferations, benign or malignant, which are of viral or non-viral origin;
(iv) bullosis or collagen disorders;
(v) chronological or UV-induced aging of the skin;
(vi) actinic keratoses and pigmentation;
(vii) stigmata of epidermal and/or dermal atrophy induced by local or systemic corticosteroids;
(viii) cutaneous atrophy;
(ix) cicatrization disorders;
(x) vibices;
(xi) promotion of cicatrization;
(xii) disorders of sebaceous function;
(xiii) general skin complaints of oral origin;
(xiv) immunological dermatological conditions; and
(xv) skin disorders associated with UV radiation exposure.

11. The method of claim 9, wherein said disorder is selected from the group consisting of common acne, comedones, polymorphonuclear leukocytes, acne rosacea, nodulocystic acne, acne conglobata, senile acne, solar, medication-related acne, occupational acne, ichthyosis, ichthyosiform states, Darier's disease, palmoplantar keratoderma, leucoplasias and leucoplasiform states, cutaneous or mucous (buccal) lichen; psoriasis, cutaneous, mucous or ungual psoriasis, psoriatic rheumatism, eczema, respiratory atopy, gingival hypertrophy, common warts, flat warts, verruciform epidermodysplasia, oral or florid papillomatoses, proliferations induced by ultraviolet radiation, basocellular or spinocellular epithelioma; corneopathies, promyelocytic leukemia, arthritis, arteriosclerosis, and hypertension.

12. A pharmaceutical composition containing a therapeutically effective amount of a compound according to claim 1.

13. A composition according to claim 12, wherein the concentration of said compound is between 0.001% and 5% by weight relative to the composition as a whole.

14. A cosmetic composition which comprises, in a cosmetically acceptable carrier or excipient, a cosmetically effective amount of at least one of the compounds as defined in claim 1.

15. A cosmetic composition according to claim 14, wherein the concentration of said compound is between 0.001% and 3% by weight relative to the composition as a whole.

16. A method of hygiene comprising administering an effective amount of a cosmetic composition as defined in claim 14, for body or hair hygiene.

17. A compound according to claim 2, which is an alkali metal, alkaline earth metal, zinc, or organic amine salt.

18. A compound according to claim 2, wherein at least one of the following is satisfied:
$R_1$ is —CO—$R_7$, and
Ar is a radical of formula (a) or (e).

19. A medicinal composition containing a medicinally effective amount of at least one compound having formula (II) according to claim 2.

20. A method of therapy which involves the administration of a therapeutically effective amount of a compound according to claim 2, wherein the condition treated is selected from the group consisting of dermatological conditions, inflammatory conditions, opthamological disorders, cancerous or precancerous conditions, alopecia, cardiovascular conditions, and insulin-dependent diabetes.

21. The method of claim 20, wherein said dermatological condition is selected from the group consisting of:
(i) conditions associated with keratinization, which optionally are associated with differentiation and/or proliferation;
(ii) keratinization disorders having an immunological and/or immunoallergic component;
(iii) dermal and epidermal proliferations, benign or malignant, which are of viral or non-viral origin;

(iv) bullosis or collagen disorders;

(v) chronological or UV-induced aging of the skin;

(vi) actinic keratoses and pigmentation;

(vii) stigmata of epidermal and/or dermal atrophy induced by local or systemic corticosteroids;

(viii) cutaneous atrophy;

(ix) cicatrization disorders;

(x) vibices;

(xi) promotion of cicatrization;

(xii) disorders of sebaceous function;

(xiii) general skin complaints of oral origin;

(xiv) immunological dermatological conditions; and (xv) skin disorders associated with UV radiation exposure.

22. The method of claim 20, wherein said disorder is selected from the group consisting of common acne, comedones, polymorphonuclear leukocytes, acne rosacea, nodulocystic acne, acne conglobata, senile acne, solar, medication-related acne, occupational acne, ichthyosis, ichthyosiform states, Darier's disease, palmoplantar keratoderma, leucoplasias and leucoplasiform states, cutaneous or mucous (buccal) lichen; psoriasis, cutaneous, mucous or ungual psoriasis, psoriatic rheumatism, eczema, respiratory atopy, gingival hypertrophy, common warts, flat warts, verruciform epidermodysplasia, oral or florid papillomatoses, proliferations induced by ultraviolet radiation, basocellular or spinocellular epithelioma; corneopathies, promyelocytic leukemia, arthritis, arteriosclerosis, and hypertension.

23. A pharmaceutical composition which comprises, in a pharmaceutically acceptable carrier, a pharmaceutically effective amount of carrier at least one compound according to claim 2.

24. A composition according to claim 23, wherein the concentration of said compound ranges from 0.001% and 5% by weight relative to the composition as a whole.

25. A cosmetic composition, which comprises, in a cosmetically acceptable carrier, at least one compounds according to claim 2.

26. A composition according to claim 25, wherein the concentration of said compound ranges from 0.001% and 3% by weight relative to the composition as a whole.

27. A method of hygiene comprising administering an effective amount of a cosmetic composition as defined in claim 25, for body or hair hygiene.

28. The propynyl bioaromatic compound of formula I, in claim 1 wherein $R_2$ and $R_3$ are taken individually and are not both alkyl radicals.

29. The propynyl bioarmoatic compound of formual I, in claim 1, wherein $R_2$ and $R_3$ together form with the adjacent aromatic ring a 5 or 6 membered ring optionally substituted with methyl groups and interrupted by a sulfur atom.

30. The propynyl bioaromatic compound of formula I which is selected from the group consisting of:

4-[3-(3,5-di-tert-betyl-4-oxo-2,5-cyclohexadien-1-ylidene)-1-propynyl]benzoic acid, 4-[3-(3,5-di-tert-betyl-4-hydroxyphenyl]-1-propynyl]benzoic acid, 2-hydroxy-4-[3-(3,5-di-tert-butyl-4-oxo -2,5-cyclohexadien-1-ylidene )-1-propynyl]benzoic acid, and 2-hydroxy-4-[3-(3,5-di-tert-butyl-4-hydroxyphenyl)-1-propynyl]benzoic acid.

31. The propynyl bioaromatic compound of formula I which the compound is 2-hydroxy-4-[3-(4,4-dimethylthiochroman-6-yl)-1-propynyl]benzoic acid.

* * * * *